US010941387B2

(12) United States Patent
Grossi De Sa et al.

(10) Patent No.: US 10,941,387 B2
(45) Date of Patent: Mar. 9, 2021

(54) ALPHA AMYLASE MUTANT INHIBITORS ISOLATED FROM PHASEOLUS VULGARIS WITH PROPERTIES OF CONTROLLING INSECT PESTS, COMPOSITIONS CONTAINING SUCH MUTANTS, AND METHOD OF USING THEREOF

(75) Inventors: Maria Fatima Grossi De Sa, Brasilia (BR); Maria Cristina Mattar Da Silva, Brasilia (BR); Rafael Perseguini Del Sarto, Brazilandia (BR); Thales Lima Rocha, Brasilia (BR)

(73) Assignee: EMPRESA BRASILEIRA DE PESQUISA AGROPECUÁRIA—EMBRAPA, Brasília (BR)

( * ) Notice: Subject to any disclaimer, the term of this patent is extended or adjusted under 35 U.S.C. 154(b) by 1076 days.

(21) Appl. No.: 14/124,538

(22) PCT Filed: Jun. 8, 2012

(86) PCT No.: PCT/BR2012/000174
§ 371 (c)(1),
(2), (4) Date: Jul. 23, 2014

(87) PCT Pub. No.: WO2012/167339
PCT Pub. Date: Dec. 13, 2012

(65) Prior Publication Data
US 2014/0366217 A1 Dec. 11, 2014

(30) Foreign Application Priority Data
Jun. 8, 2011 (BR) .............................. PI1102841-6

(51) Int. Cl.
| C12N 9/24 | (2006.01) |
| C12N 15/82 | (2006.01) |
| C12N 9/26 | (2006.01) |
| C07K 14/415 | (2006.01) |
| A01N 65/20 | (2009.01) |

(52) U.S. Cl.
CPC ....... *C12N 9/2414* (2013.01); *C12N 15/8286* (2013.01); *A01N 65/20* (2013.01); *C07K 14/415* (2013.01); *C12N 2840/007* (2013.01); *Y02A 40/146* (2018.01)

(58) Field of Classification Search
CPC .......................... C12N 9/2414; C12N 15/8286
See application file for complete search history.

(56) References Cited

U.S. PATENT DOCUMENTS

| 5,338,544 A * | 8/1994 | Donovan | ............... | C12N 15/75 |
| | | | | 424/93.2 |
| 7,019,197 B1 * | 3/2006 | Christou | .............. | C07K 14/325 |
| | | | | 435/320.1 |
| 2010/0311645 A1 * | 12/2010 | Rech Filho | ...... | C07K 14/43518 |
| | | | | 514/2.3 |

FOREIGN PATENT DOCUMENTS

JP  07132092  *  5/1995

OTHER PUBLICATIONS

Fozo et al (Small Toxic Proteins and the Antisense RNAs That Repress Them. Microbiology and Molecular Biology Reviews, 72: p. 579-589, 2008).*
Sharma et al (Genetic transformation of crop plants: Risks and opportunities for the rural poor Current Science, vol. 80, No. 12, 1495-1506, Jun. 25, 2001).*
Fozo et al (Small Toxic Proteins and the Antisense RNAs That Repress Them. Microbiology and Molecular Biology Reviews, 72: p. 579-589, 2008) (Year: 2008).*
Sharma et al (Genetic transformation of crop plants: Risks and opportunities for the rural poor Current Science, vol. 80, No. 12, 1495-1506, Jun. 25, 2001) (Year: 2001).*
Campbell et al (Post-translational modifications of alpha-amylase inhibitor-1 from the common bean, Phaseolus vulgaris, vary with transgenic expression in other legumes) Sequences submitted (Oct. 2006) to the EMBL/GenBank/DDBJ databases, published in 2007. (Year: 2007).*
International Preliminary Report on Patentability, issued in PCT/BR2012/00174 by the International Bureau, with Written Opinion, dated Jan. 22, 2013.
International Search Report for PCT/BR2012/00174, dated Jan. 22, 2013.
Campbell et al., "Phaseolus vulgaris cultivar Cannillini alpha amylase inhibitor-1 precursor, gene, complete cds", GenBank Acession EF087992.1, dated Nov. 26, 2006.
Grossi-De-Sa et al., "Molecular evolution of alpha-amylase inhibitor: screening for cotton boll weevil, *Anthonomus grandis*", Abstract L3-017P, pp. 511-512 (2005).

(Continued)

*Primary Examiner* — Ashley K Buran
*Assistant Examiner* — Wayne Zhong
(74) *Attorney, Agent, or Firm* — Sughrue Mion, PLLC

(57) ABSTRACT

The present invention relates to the field of insect pests control, using methods and compositions which comprise of alpha-amylase analogous mutant inhibitors (αAIs). More specifically, the invention provides new αAIs analogous mutant molecules for controlling insect pests, in particular boll weevils (*Anthonomus grandis*), partially or totally presenting reduction of the amylolytic activity of the digestive enzymes in the intestinal lumen of the insect. Other aspects of the invention include gene constructs containing the nucleic acid molecules that code for the alpha-amylase inhibitors, heterologous expression methods of the new molecules in the active form, and the use of these molecules for controlling insect pests. The invention also provides analogous synthetic genes optimized for their transformation and expression in plants.

40 Claims, 7 Drawing Sheets
Specification includes a Sequence Listing.

(56) References Cited

OTHER PUBLICATIONS

Silva et al: "Evolução molecular in vitro de inibidores de α-amilases: Especificidade e interação e aplicação no controle de pragas de importância econômica", I. Workshop de interação molecular planta-pragas, 13 e, pp. 17-22 (Dec. 14, 2004).
Del Sarto et al., "Seleção de Inibidores de alfa-amylâses especificos para o controle do bicudo do algodoeiro", V. Congresso Brasileiro do Algodão (2005).

\* cited by examiner

SEQUENCE LISTING

```
<160> NUMBER OF SEQ ID NOS: 15

<210> SEQ ID NO 1
<211> LENGTH: 666
<212> TYPE: DNA
<213> ORGANISM: Phaseolus vulgaris

<400> SEQUENCE: 1
gccaccgaaa cctccttcat catcgatgcg ttcaacaaaa ccaaccttat ccttcaaggc      60
gatgccaccg tctcatccaa cggcaactta caactatcct ataattcata cgactctatg     120
agcagagcct tctactccgc ccccatccaa atcagggaca gcaccaccgg caacgtcgcc     180
agcttcgaca ccaacttcac aatgaatatc cgcactcacc gccaagcaaa ttccgccgtt     240
ggccttgact ttgttctcgt ccccgtccag cccgaatcca aaggcgatac tgtgactgtg     300
```

```
gagttcgaca ccttcctcag ccgtattagc atcgacgtga acaacaacga tatcaaaagc    360
gtgccttggg atgtacacga ctacgacgga caaaacgccg aggttcggat cacctataac    420
tcctccacga aggtcttggc ggtttctctg tcaaacccctt ctacgggaaa gagcaacgag   480
gtctctgcca gaatggaggt ggagaaagaa cttgacgact gggtgagggt tgggttctct    540
gccatctcag gggttcatga atatagcttt gaaacgagag acgtgctctc ttggtctttt    600
tcttccaagt tctcccaaca caccacatct gaacgttcca acatcctcct caacaagatc    660
ctctag                                                               666

<210> SEQ ID NO 2
<211> LENGTH: 666
<212> TYPE: DNA
<213> ORGANISM: Phaseolus vulgaris

<400> SEQUENCE: 2
gccaccgaaa cctccttcat catcgatgcg ttcaacaaaa ccaaccttat cctccaaggc    60
gatgccaccg tctcatccaa aggctactta caactacata cagtggactc tatgtgcagc    120
gccttctact ccgcccccat ccaaatcagg acagcacca ccggcaacgt cgccagcttc     180
gacaccaact tcacaatgaa tattcgcact caccgccaag caaattccgc cgttggcctt    240
gactttgttc tcgtccccgt ccagcccgaa tccaaaggcg atactgtgac tgtggagttc    300
gacaccttcc gcagccgtat tagcatcgac gtgaacaaca acgatatcaa agcgtgcct    360 tgggatgtac acgactacga cggacaaaac gccgaggttc ggatcaccta taactcctcc    420
acgaaggtct tctcggtttc tctgtcaaac ccttctacgg gaaagagcaa caacgtctct    480
accacagtgg agctggagaa agaagtttac gactgggtga gcgttgggtt ctctgccacc    540 tcagggggctt atcaatggag ctatgaaacg cacgacgtcc tctcttggtc ttttctcttcc   600 aagttcatca atcttaagga ccaaaaatct gaacgttcca acatcgtcct caacaagatc    660
ctctag                                                               666

<210> SEQ ID NO 3
<211> LENGTH: 666
<212> TYPE: DNA
<213> ORGANISM: Phaseolus vulgaris

<400> SEQUENCE: 3
gccaccgaaa cctccttcat catcgatgcg ttcaacgaaa ccaaccttat cctccaaggc    60
gatgccaccg tctcatccaa aggctactta caactacata cagtggactc tatgtgcagc    120
gccttctact ccgcccccat ccaaatcagg acagcacca ccggcaacgt cgccagcttc     180
gacaccaact tcacaatgaa tatcaccact caacgcgaag caaattccgt cattggcctt    240
gactttgctc tcgtccccgt ccagcccaaa tccaaaggcc atactgtgac tgtgcagttc    300
gacaccttcc gcagccgtat tagcatcgac gtgaacaaca acgatatcaa agcgtgcct    360 tgggatgaac aggactacga cggacaaaac gccaaggttc ggatcaccta taactcctcc    420
acgaaggtct tctcggtttc tctgtcaaac ccttctacgg gaaagagcaa caacgtctct    480
accacagtgg agctggagaa agaagtttac gactgggtga gcgttgggtt ctctgccacc    540 tcagggggctt atcaatggag ctatgaaacg cacgacgtcc tctcttggtc ttttctcttcc   600 aagttcatca atctaaagga ccaaaaatct gaacgtttca acatcgtcct caacaagatc    660
ctctag                                                               666
```

<210> SEQ ID NO 4
<211> LENGTH: 221
<212> TYPE: PRT
<213> ORGANISM: Phaseolus vulgaris

<400> SEQUENCE: 4

Ala Thr Glu Thr Ser Phe Ile Ile Asp Ala Phe Asn Lys Thr Asn Leu
1               5                   10                  15

Ile Leu Gln Gly Asp Ala Thr Val Ser Ser Asn Gly Asn Leu Gln Leu
            20                  25                  30

Ser Tyr Asn Ser Tyr Asp Ser Met Ser Arg Ala Phe Tyr Ser Ala Pro
        35                  40                  45

Ile Gln Ile Arg Asp Ser Thr Thr Gly Asn Val Ala Ser Phe Asp Thr
    50                  55                  60

Asn Phe Thr Met Asn Ile Arg Thr His Arg Gln Ala Asn Ser Ala Val
65                  70                  75                  80

Gly Leu Asp Phe Val Leu Val Pro Val Gln Pro Glu Ser Lys Gly Asp
                85                  90                  95

Thr Val Thr Val Glu Phe Asp Thr Phe Leu Ser Arg Ile Ser Ile Asp
            100                 105                 110

Val Asn Asn Asn Asp Ile Lys Ser Val Pro Trp Asp Val His Asp Tyr
        115                 120                 125

Asp Gly Gln Asn Ala Glu Val Arg Ile Thr Tyr Asn Ser Ser Thr Lys
    130                 135                 140

Val Leu Ala Val Ser Leu Ser Asn Pro Ser Thr Gly Lys Ser Asn Glu
145                 150                 155                 160

Val Ser Ala Arg Met Glu Val Glu Lys Glu Leu Asp Asp Trp Val Arg
                165                 170                 175

Val Gly Phe Ser Ala Ile Ser Gly Val His Glu Tyr Ser Phe Glu Thr
            180                 185                 190

Arg Asp Val Leu Ser Trp Ser Phe Ser Ser Lys Phe Ser Gln His Thr
        195                 200                 205

Thr Ser Glu Arg Ser Asn Ile Leu Leu Asn Lys Ile Leu
    210                 215                 220

<210> SEQ ID NO 5
<211> LENGTH: 221
<212> TYPE: PRT
<213> ORGANISM: Phaseolus vulgaris

<400> SEQUENCE: 5

Ala Thr Glu Thr Ser Phe Ile Ile Asp Ala Phe Asn Lys Thr Asn Leu
1               5                   10                  15

Ile Leu Gln Gly Asp Ala Thr Val Ser Ser Lys Gly Tyr Leu Gln Leu
            20                  25                  30

His Thr Val Asp Ser Met Cys Ser Ala Phe Tyr Ser Ala Pro Ile Gln
        35                  40                  45

Ile Arg Asp Ser Thr Thr Gly Asn Val Ala Ser Phe Asp Thr Asn Phe
    50                  55                  60

Thr Met Asn Ile Arg Thr His Arg Gln Ala Asn Ser Ala Val Gly Leu
65                  70                  75                  80

Asp Phe Val Leu Val Pro Val Gln Pro Glu Ser Lys Gly Asp Thr Val
                85                  90                  95

Thr Val Glu Phe Asp Thr Phe Arg Ser Arg Ile Ser Ile Asp Val Asn
            100                 105                 110

Asn Asn Asp Ile Lys Ser Val Pro Trp Asp Val His Asp Tyr Asp Gly

```
                115                 120                 125
Gln Asn Ala Glu Val Arg Ile Thr Tyr Asn Ser Ser Thr Lys Val Phe
    130                 135                 140

Ser Val Ser Leu Ser Asn Pro Ser Thr Gly Lys Ser Asn Asn Val Ser
145                 150                 155                 160

Thr Thr Val Glu Leu Glu Lys Glu Val Tyr Asp Trp Val Ser Val Gly
                165                 170                 175

Phe Ser Ala Thr Ser Gly Ala Tyr Gln Trp Ser Tyr Glu Thr His Asp
                180                 185                 190

Val Leu Ser Trp Ser Phe Ser Ser Lys Phe Ile Asn Leu Lys Asp Gln
                195                 200                 205

Lys Ser Glu Arg Ser Asn Ile Val Leu Asn Lys Ile Leu
    210                 215                 220

<210> SEQ ID NO 6
<211> LENGTH: 221
<212> TYPE: PRT
<213> ORGANISM: Phaseolus vulgaris

<400> SEQUENCE: 6

Ala Thr Glu Thr Ser Phe Ile Ile Asp Ala Phe Asn Glu Thr Asn Leu
1               5                   10                  15

Ile Leu Gln Gly Asp Ala Thr Val Ser Ser Lys Gly Tyr Leu Gln Leu
                20                  25                  30

His Thr Val Asp Ser Met Cys Ser Ala Phe Tyr Ser Ala Pro Ile Gln
                35                  40                  45

Ile Arg Asp Ser Thr Thr Gly Asn Val Ala Ser Phe Asp Thr Asn Phe
    50                  55                  60

Thr Met Asn Ile Thr Thr Gln Arg Glu Ala Asn Ser Val Ile Gly Leu
65                  70                  75                  80

Asp Phe Ala Leu Val Pro Val Gln Pro Lys Ser Lys Gly His Thr Val
                85                  90                  95

Thr Val Gln Phe Asp Thr Phe Arg Ser Arg Ile Ser Ile Asp Val Asn
                100                 105                 110

Asn Asn Asp Ile Lys Ser Val Pro Trp Asp Glu Gln Asp Tyr Asp Gly
                115                 120                 125

Gln Asn Ala Lys Val Arg Ile Thr Tyr Asn Ser Ser Thr Lys Val Phe
    130                 135                 140

Ser Val Ser Leu Ser Asn Pro Ser Thr Gly Lys Ser Asn Asn Val Ser
145                 150                 155                 160

Thr Thr Val Glu Leu Glu Lys Glu Val Tyr Asp Trp Val Ser Val Gly
                165                 170                 175

Phe Ser Ala Thr Ser Gly Ala Tyr Gln Trp Ser Tyr Glu Thr His Asp
                180                 185                 190

Val Leu Ser Trp Ser Phe Ser Ser Lys Phe Ile Asn Leu Lys Asp Gln
                195                 200                 205

Lys Ser Glu Arg Phe Asn Ile Val Leu Asn Lys Ile Leu
    210                 215                 220

<210> SEQ ID NO 7
<211> LENGTH: 222
<212> TYPE: PRT
<213> ORGANISM: Phaseolus vulgaris

<400> SEQUENCE: 7

Ala Thr Glu Thr Ser Phe Ile Ile Asp Ala Phe Asn Lys Thr Asn Leu
```

```
                1               5                      10                      15
            Ile Leu Gln Gly Asp Ala Thr Val Ser Ser Asn Gly Asn Leu Gln Leu
                            20                      25                      30
            Ser Tyr Asn Ser Tyr Asp Ser Met Ser Arg Ala Phe Tyr Ser Ala Pro
                        35                      40                      45
            Ile Gln Ile Arg Asp Ser Thr Thr Gly Asn Val Ala Ser Phe Asp Thr
                    50                      55                      60
            Asn Phe Thr Met Asn Ile Arg Thr His Arg Gln Ala Asn Ser Ala Val
            65                      70                      75                      80
            Gly Leu Asp Phe Val Leu Val Pro Val Gln Pro Glu Ser Lys Gly Asp
                                85                      90                      95
            Thr Val Thr Val Glu Phe Asp Thr Phe Leu Ser Arg Ile Ser Ile Asp
                            100                     105                     110
            Val Asn Asn Asp Ile Lys Ser Val Pro Trp Asp Val His Asp Tyr Asp
                        115                     120                     125
            Gly Gln Asn Ala Glu Val Arg Ile Thr Tyr Asn Ser Ser Thr Lys Val
                    130                     135                     140
            Phe Ser Val Ser Leu Ser Asn Pro Ser Thr Gly Lys Ser Asn Asn Val
            145                     150                     155                     160
            Ser Thr Thr Val Glu Leu Glu Lys Glu Val Tyr Asp Trp Val Ser Val
                                165                     170                     175
            Gly Phe Ser Ala Thr Ser Gly Ala Tyr Gln Trp Ser Tyr Glu Thr His
                            180                     185                     190
            Asp Val Leu Ser Trp Ser Phe Ser Ser Lys Phe Ile Asn Leu Lys Asp
                        195                     200                     205
            Gln Lys Ser Glu Arg Ser Asn Ile Val Leu Asn Lys Ile Leu
                    210                     215                     220

<210> SEQ ID NO 8
<211> LENGTH: 219
<212> TYPE: PRT
<213> ORGANISM: Phaseolus vulgaris

<400> SEQUENCE: 8

Ala Ser Asp Thr Ser Phe Asn Phe Tyr Ser Phe Asn Glu Thr Asn Leu
            1               5                      10                      15
            Ile Leu Gln Gly Asp Ala Thr Val Ser Ser Lys Gly Tyr Leu Gln Leu
                            20                      25                      30
            His Thr Val Asp Ser Met Cys Ser Ala Phe Tyr Ser Ala Pro Ile Gln
                        35                      40                      45
            Ile Arg Asp Ser Thr Thr Gly Asn Val Ala Ser Phe Asp Thr Asn Phe
                    50                      55                      60
            Thr Met Asn Ile Thr Thr Gln Arg Glu Ala Asn Ser Val Ile Gly Leu
            65                      70                      75                      80
            Asp Phe Ala Leu Val Pro Val Gln Pro Lys Ser Lys Gly His Thr Val
                                85                      90                      95
            Thr Val Gln Phe Asp Thr Phe Arg Ser Arg Ile Ser Ile Asp Val Asn
                            100                     105                     110
            Asn Asn Asp Ile Lys Ser Val Pro Trp Asp Glu Gln Asp Tyr Asp Gly
                        115                     120                     125
            Gln Asn Ala Lys Val Arg Ile Thr Tyr Asn Ser Ser Thr Lys Val Leu
                    130                     135                     140
            Ala Val Ser Leu Ser Asn Pro Ser Thr Gly Lys Ser Asn Glu Val Ser
            145                     150                     155                     160
```

Ala Arg Met Glu Val Glu Lys Glu Leu Asp Asp Trp Val Arg Val Gly
            165                 170                 175

Phe Ser Ala Ile Ser Gly Val His Glu Tyr Ser Phe Thr Arg Asp
        180                 185                 190

Val Leu Ser Trp Ser Phe Ser Ser Lys Phe Ser Gln His Thr Thr Ser
        195                 200                 205

Glu Arg Ser Asn Ile Leu Leu Asn Lys Ile Leu
    210                 215

<210> SEQ ID NO 9
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(9)
<223> OTHER INFORMATION: n is a, c, g, or t

<400> SEQUENCE: 9
ggccnnnnng gcc                                                        13

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 10
cccggcccag gcggccgcca ccgaaacctc                                      30

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 11
cccggcccag gcggccgcca gcgacacctc                                      30

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 12
ccggccggcc tggccgagga tcttgttgag                                      30

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
ccggccggcc tggccgagga tattgttgag                                      30

<210> SEQ ID NO 14
<211> LENGTH: 87

```
<212> TYPE: DNA
<213> ORGANISM: Artificial Sequence
<220> FEATURE:
<223> OTHER INFORMATION: Synthetic oligonucleotide

<400> SEQUENCE: 14 cccccggga tggcttcctc caacttactc tccctagccc tcttccttgt gcttctcaac      60
cacgcaaact cagccaccga aacctcc                                         87

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
cccgagctct tagaggatct tgttgaggac                                      30
```

ALPHA AMYLASE MUTANT INHIBITORS ISOLATED FROM PHASEOLUS VULGARIS WITH PROPERTIES OF CONTROLLING INSECT PESTS, COMPOSITIONS CONTAINING SUCH MUTANTS, AND METHOD OF USING THEREOF

CROSS REFERENCE TO RELATED APPLICATIONS

This application is a National Stage of International Application No. PCT/BR2012/000174 filed Jun. 8, 2012, claiming priority based on Brazilian Patent Application No. PI1102841-6, filed Jun. 8, 2011, the contents of all of which are incorporated herein by reference in their entirety.

FIELD OF THE INVENTION

The present invention relates to the field of insect pests control, using methods and compositions which comprise analogous mutants of alpha-amylase inhibitors (αAIs). More specifically, the invention provides new αAIs analogous mutant molecules for controlling insect pests, in particular boll weevils (*Anthonomus grandis*), partially or totally reducing the amylolytic activity of the digestive enzymes in the intestinal lumen of the insect. Other aspects of the invention include gene constructs containing the nucleic acid molecules that code for the alpha-amylase inhibitors, heterologous expression methods of the new molecules in the active form, and the use of these molecules for controlling insect pests. The invention also provides analogous synthetic genes optimized for their transformation and expression in plants.

BACKGROUND OF THE INVENTION

Insect pests are the main factor in the production losses of important species in the worldwide agriculture. For instance, damage caused exclusively by boll weevil can be economically devastating for cotton producers in the countries where said insect can be found, reaching millions of dollars.

The traditional methods of controlling populations of insect pests are crop rotation and application of chemical and synthetic pesticides on a larger scale. However, the government and consumers have enfaticaly highlighted the environmental and health damage the use of chemical pesticides brings. The regulations on the production and use of said chemical agents are provided by the laws that aim at restricting the use of said agents and punishing the users. Thus, the development of alternatives to the use of chemical pesticides is considerably interesting. The biological control of insect pests of significance for the agriculture, such as fungus, bacteria and other species of insects—despite being a friendly and commercially attractive alternative—not always results in the efficiency desired.

The cotton plant is host of a large number of insects, and at least 20 species of insects are potentially harmful (Papa, G. In *Algodão: Pesquisas e Resultado para o campo* v. 01, 2006). One of the main insect pests is the boll weevil, *Anthonomus grandis* (Boheman, C. H. Description of new species. In Schoenherr, Genera et species *Curculionidum cum synonymia hujus* Familiae, vol. 7, pt. 2. Paris: Roret. 461 p., 1843), considered one of the most harmful cotton crop pests, found in Mexico, Cuba, Haiti, Venezuela, Columbia, Paraguay and Brazil. Said insect feeds off and develops in buds and fruit of the host, causing direct damage to the commerce of cotton fiber. The infestation levels rapidly increase and damage can reach up to 100% of the production if proper control measures are not taken. It represents a great damage potential and is considered a key-pest to planning and controlling crop-harming insects, mainly due to the difficulty in controlling them with chemical insecticides.

Cotton plants and insect pests coexist for a long evolutionary period. Plants and insect form an interdependent, competitive morphological and biochemical system, resulting—most of the times—in the use of part of the plant by the insect. That part of the plant is the damage caused by the insect, and depends on how large is the population of insects and on the plant's resistance to such an attack and its capability to recover from said damage (Beltrao, E. M., Souza, J. G. *O agronegócio do algodão no Brasil*. Embrapa: Brasilia, v. 01, 1999).

The plant-versus-insect interaction can be visualized from two aspects: from the insect's point of view, wherein the plant varies from adequate to completely inadequate as a host; and on the other hand, from the plant's point of view, wherein the smaller the number of species and abundance of insects associated therewith and the weaker the effect said insects exert on them, the greater the resistance to said insects (Santos, W. J. *Identificação, biologia, amostragem e controle das pragas do algodoeiro*. In: Embrapa Agropecuária Oeste; Embrapa Algodão. *Algodão: tecnologia de produção*., p. 296 p. 2002).

Regarding plant's resistance to insect pests, there is a complete and extensive arsenal of mechanisms to attack and counterattack insects' activity, ranging from a mere morphological complication to complex phytochemical components, which directly interfere with the metabolic process involved in the use of the plant as a host to the insect. In practice the cotton plant's resistance to insect pests represents the capability of certain cultivars to produce algodão of better quality in larger amounts than other cultivars, under the attack of the same population of insect pests (Freire, E. C. *Cultivares e produção de semente na melhoria da qualidade do algodão no nordeste e centro-oeste do Brasil. Boletim informativo Embrapa* (Embrapa Journal)/CNPA. 1997).

In most of the countries where cotton is cultivated, the vulnerability of the insect pests represents the main problem of said culture. Without more effective control alternatives, producers keep believing that chemical insecticides are the only way to protect the crops. In spite of being effective, they are expensive and potentially harmful to man, to the environment and, in the long term, disrupt the resistance processes, leading to the resurgence of pests and reduction on the number of natural enemies (Panizzi, A. R. *Efeito de inseticidas na população das principals pragas da soja*. An. Soc. Entomol. Brazil, v. 6, p. 264-275. 1977).

The stable insertion of exogenous genes in cotton plants, aiming at inducing the plant to defend against insect pests is considered an alternative to the decrease of the major part of the problems associated with the chemical methods. Said technology has several advantages, including the fact it does not pollute the environment. Different statements show genetically transformed plants modified with protein inhibitors, wherein no negative effects on the environment have been noticed and the characteristics are inheritable and normally expressed in the plant (Carpenter, J. Peer reviewed surveys indicate positive impacto of commercialized GM crops. Nature Biotechnology. 28:319-321, 2010; Quirino, B.; In *Revolução dos transgênicos*. Interciência Ltda. 2008; Kluh, I.; Horn, M.; Hýblová, J.; Hubert, J.; Maresová, L. D.; Voburka, Z.; Kudliková, I.; Kocourek, F.; Mares, M.; Inhbitory specificity and insecticidal selectively of α-amylase inhibitor from *Phaseolus vulgaris*. Phytochemistry, 66:31-39. 2005; Schuler, T.; Poppy, G. M.; Kerry, B. R.; Denholm, I. Insect Resistant Transgenic Plants. Trends in Biotechnology, 16:168-175. 1998). The use of protein inhibitors found in nature having biotechnological applicability is quite vast, and said inhibitors are an important source of raw materials for the development of new products intended, for instance, for inactivate enzymes in the bowel of insects covering a broad spectrum of action. The alpha-amylase inhibitor (αAIs) was a great discovery in the group of protein inhibitors. That kind of inhibitor can be isolated from different sources. The alpha-amylase inhibitor found in common beans (*Phaseolus vulgaris*) has a great transgenic potential aiming for the protection of plants against insects, mainly coleoptera—Bruchidae (Morton, R. L.; Shoroeder, H. E.; Bateman, K. S.; Chrispeels, M. J.; Armstrong, E.; Higgins, T. J. (2000) Bean alpha-amylase inhibitor 1 in transgenic peãs (*Pisum sativum*) provides complete protection from pea weevil (*Bruchus pisorium*) under field conditions. Proceedings of the National Academy of Sciences of the United States of America, 97, 3820-3825, 2000). Although the grains of common beans have at least three isoforms of (αAIs), called isoform 1 (αAI-1); isoform 2 (αAI-2) and one precussor form (αAIL), extensive research is carried out on isoforms αAI-1 and αAI-2, which are deemed potential source of molecules for biotechnological programs, intended for producing insect pest-resistant transgenic plants. With such a strategy it is possible for one to reduce the populations of insect pests at acceptable levels to the economical interest. In general, αAI-1 inhibitor can be found in beans all over the world (Iguti, A. M.; Lajolo, F. M. Isolation and Purification of Amylase Inhibitors from Beans. In: PAABS—The Pan-American Association of Biochemical Societies—VI Congress. Sao Paulo, 1990, Sao Paulo. PAABS—The Pan-American Association of Biochemical Societies—VI Congress, 1990; Suzuki K, Ishimoto M, Kitamura K. cDNA sequence and deduced primary structure of an alpha-amylase inhibitor forma a bruchid-resistant wild common bean. Biochim Biophys Acta. 1206:289-291.1994; Suzuki K., Ishimoto M., Kikuchi F., Kitamura K. Growth inhibitory effect of an α-amylase inhibitor from the wild common bean resistant to the Mexican bean weevil (*Zabrotes subfasciatus*). Jpn J Breed 43:257-265, 1993; Ishimoto, M., Sato, T., Chrispeels, M. J.; Kitamura, K. Bruchid resistance of transgenic azuki bean expressing seed α-amylase inhibitor of common bean. Entomol. Exp. Appl., 79, 309-315.1996). The protein accumulates in the seeds and represents 9-11% of the total protein of the seeds (Moreno, J.; Chrispeels, M. J. A Lectin gene encodes the alpha-amylase inhibitor of the common bean. Proceeding of the National Academy Science 86:7885-7889, 1989), may vary according to the limits imposed by the extraction methods. αAI-1 and αAI-2 inhibitors belong in the lectin family, and the structure of the native molecule is in the tetrameric form ($α_2β_2$), comprising two α sub-units and two β sub-units. The inhibitor is synthesized in the endoplasmic reticulum, modified in the Golgi apparatus by removing the signal peptide, glycated and transported to the storage vacuoles where it undergoes proteolytic processing in order to become an active molecule (Moreno, J.; Chrispeels, M. J. *A Lectin gene encodes the alpha-amylase inhibitor of the common bean.* Proceeding of the National Academy Science 86:7885-7889, 1989; Moreno, J.; Altabella T.; Chrispeels, M. J. Characterization of alpha-amylase-inhibitor, a lectin-like protein in the seeds of *Phaseolus vulgaris*. Plant Phisiololgy 92 703-709.1990; Pueyo, J. J.; Hunt, D. C.; Chrispeels, J. M. Activation of bean (*P. vulgaris*) alpha amylase inhibitors requires proteolytic processing of the preprotein. Plant Physiology, 101:1341-1348, 1993; Young, N. M.; Thibault, P., Watson, D. C.; Chrispeels, M. J. Post translational processing of two alpha-amyalase inhibitors and an arcelin from the common bean, *P. vulgaris*. FEBS Letters, 5: 203-20, 1999). Said inhibitors have a broad spectrum of action involving specificity issues. While αAI-1 inhibits mammal alpha-amylases and strongly some insect alpha-amylases, such as *Callosobruchus maculatus* and *C. chinensis; Bruchus pisorium* (Franco, O. L.; Rigden, D. J.; Melo, F. R.; Grossi-De-Sá, M. F. Plant alpha-amylase inhibitors and their interaction with insect alpha-amyalses. European Journal of Biochemistry, 269: 397-412, 2002) and *Hypothenemus hampei* (Valencia, A.; Bustillo, A. E.; Ossa, G. E.; Chrispeels, J. M. Alpha-amyalse of coffe Berry borer (*Hypothenemus hampei*) and their inhibition by two plant amylase inhibitors. Insect Biochemistry and Molecular Biology, 30:207-213, 2000), the αAI-2 form, found only in non-marketed beans, strongly inhibits only the *Z. subfasciatus* alpha-amylase (important common bean pest) and does not inhibit pig pancreatic alpha-amylase (PPA) (Grossi de Sá, M. F., Mirkov, T. E., Ishimoto, M., Colucci, G., Bateman, K. S., Chrispeels, M. J. Molecular Characterization of a bean alpha-amylase inhibitor that inhibits alpha-amylase of the Mexican bean weevil *Z. subfasciatus*. Planta. 203:295-303, 1997; Silva, M. C. M.; Mello, L. V.; Coutinho, M. V.; Rigden, D. J.; Neshich, G.; Chrispeels, M. J.; Grossi-de-Sá, M. F. Mutants of common bean alpha-amylase inhibitor-2 as an approach to investigate binding specificity to alpha-amylases. *Pesquisa Agropecuária Brasileira*, 39:201-208). Tested against *A. grandis*, original inhibitors αAI-1 and αAI-2, which have in common 78% amino acid sequence identity, do not exhibit anti-amylase activity (Oliveira-Neto O B, Batista J A, Rigden D J, Franco O L, Falcão R, Fragoso R R, Mello L V, dos Santos R C, Grossi-de-Sá M F. Molecular cloning of alpha-amylases from cotton boll weevil, *Anthonomus grandis* and structural relation to plant inhibitor: an approach to insect plant resistance. Journal Protein Chemistry. 2003 22:77-87, 2003). Moreover, said inhibitors do not exhibit activity against the endogenous amylases of plants (Moreno, J.; Chrispeels, M. J. *A Lectin gene encodes the alpha-amylase inhibitor of the common bean*. Proceeding of the National Academy Science 86:7885-7889, 1989).

Alpha-amylases (α-1,4-glucan-4-glucanohidrolase, EC 3.2.1.1—http://www.chem.gmul.ac.uk/iubmb/enzyme/rules.html) are enzymes from a group largely present in secretions of microorganisms, animals and plants and which catalyze, mainly, the hydrolysis of α-1,4 glycosidic bonds, into starch, glycogen and several oligosaccharides (Svensson, B. Protein engeenering in the alpha-amylase family: catalytic mechanism, substrate specificity and stability, Plant Molecular Biology 25:141-157, 1994). Some alpha-amylases can exclusively break α-1,6 or α-1,4/α-1,6 glycosidic bonds; some can cleve sucrose residues, and some can even hydrolize a form of trehalose-bonded glucose (MacGregor, E. A. Alpha-amylase structure and activity. J. Protein Chem 7:399-415, 1988). The clevage of starch by alpha-amylases is the first step of the enzymatic degradation of polysaccharides, which is essential for the assimilation of carbohydrates. In insects, the inhibition of the amyolytic activity reduces the assimilation of carbohydrates, thus causing a decrease in larva growth and bringing damage to the whole life cycle, and may lead to death by starvation (Oliveira-Neto, O. B.; Batista, J. A. N.; Ridgen, D. J.; Franco, O. L.; Falcão, R.; Fragoso, R. R.; Mello, L. V.; Santos, R. C.;

Grossi-de Sá, M. F. Molecular cloning of α-amylases from cotton boll weevil, *A. grandis* and structural relations of plant inhibitors: an approach to insect resistance. Journal of Protein Chemistry, 22:77-87, 2003. Kluh, I.; Horn, M.; Hýblová, J.; Hubert, J.; Maresová, L. D.; Voburka, Z.; Kudliková, I.; Kocourek, F.; Mares, M.; Inhbitory specificity and insecticidal selectively of α-amylase inhibitor from *Phaseolus vulgaris*. Phytochemistry, 66:31-39. 2005).

Several alpha-amylase inhibitors had their tridimensional structure determined either in an isolated way or in complex with alpha-amylases, for instance, the *Amaranthus hipochondriacus* inhibitor (Lu, S., Deng, P., Liu, X., Luo, J., Han, R., Gu, X., Liang, S., Wang, X., Li, F., Lozanov, V., Patthy, A., Pongor, S., Solution structure of the major alpha-amylase inhibitor of the crop plant amaranth. Journal of Biological Chemistry, 274:20473-20478. 1999; Martins, J. C.; Enassar, M.; Willem, R.; Wieruzeski, J. M.; Lippens, G.; Wodak, S. J. Solution structure of the main alpha-amylase inhibitor from amaranth seeds. European Journal of Biochemistry, 268:2379-2389. 2001) and the isolated rye inhibitor (Iulek, J., Franco, O. L., Silva, M., Slivinski, C. T., Bloch, C., Jr., Rigden, D. J., Grossi-de-Sá, M. F. Purification, biochemical characterisation and partial primary structure of a new alpha-amylase inhibitor from *Secale cereale* (rye) Int. J. Bio-chem. Cel. Biol 32: 1195-1204. 2000). The *P. vulgaris* αAI-1 inhibitor had its atomic structure determined in complex with mammal alpha-amylase (PPA) and *Tenebrio molitor* alpha-amylase (Nahoum V, Farisei F, Le-Berre-Anton V, Egloff M P, Rougé P, Poerio E, Payan F. A plant seed inhibitor of two classes of alpha-amylase in complex with the bean *P. vulgaris* inhibitor. Acta Crystallogr D Biol Crystallogr. 55:360-362. 1999). The formation of the enzyme-inhibitor complexes as in the case of αAI-1 is totally dependent upon the protein concentration, temperature and pH (Grossi de Sá, M. F., Mirkov, T. E., Ishimoto, M., Colucci, G., Bateman, K. S., Chrispeels, M. J. Molecular Characterization of a bean alpha-amylase inhibitor that inhibits alpha-amylase of the Mexican bean weevil *Z. subfasciatus*. Planta. 203:295-303, 1997).

Inserting a gene coding for αAI-1 inhibitor has conferred resistance to several bruchid insects when expressed in transgenic pea (*Pisum sativum* L.) seeds (Shade, R. E., Schroeder, R. E., Pueyo, J. J., Tabe, L. M., Murdock, L. I., Higgins, T. J. V., Chrispeels, J. M. Transgenic pea seeds expressing the α-amylase inhibitor of the common bean are resistant to bruchid beetles. Biotechnology 12:793-796, 1994; Schroeder, R. E., Gollash, S., Moore, A. Bean α-amylase inhibitor confers resistance to the pea weevil (*Bruchus pisorium*) in transgenic peas (*Pisum sativum* L.). Plant Physiology 107:1233-1239, 1995); Morton, R. I., Schroeder, R. E., Bateman, K. S., Chrispeels, J. M.; Armostrong, E., Higgins, T. J. V. Bean α-amylase inhibitor 1 in transgenic peas (*Pisum sativum* L.) provides complete protection from pea weevil (*Bruchus pisorium*) under field conditions. Proc. Nac. Acad. Sci. USA 97:3820-3835, 2000; Sousa-majer, M. J. D., Hardei, D. C.; Turner, N. C., Higgins, T. J. V. (2007) Bean α-amylase inhibitors in transgenic peas inhibit development of pea weevil larvae. J. Econ, Entomol. 100:1416-1422) in azuki bean (Ishimoto, M., Sato, T., Chrispeels, M. J., Kitamura, K. (1996) Bruchis resistance of transgenic azuki bean expressing seeds α-amylase inhibitor of the common bean. Entomol. Exp. Appl. 79:309-315) in chick pea seed (*Cicer arietimun*) (Sarmah, B. K., Moore, A., Tate, W., Molvig, L., Morton, R. L., Rees, D. P., Chiasise, P., Chrispeels, J. M., Tae, L. M., Higgins, T. J. V. (2004) Transgenic chickpea seeds expressing high levels of a bean α-amylase inhibitor. Mol. Breed 14:73-82; Ignacimuthu, S. Prakash, S. (2006) Agrobacteirum-mediated transformation of chickpea with α-amylase inhibitor gene for insect resistance. J. Biosci 31:339-345; in *Vigna radiata* L. plants (Sonia, R. S., Singh, R. P., Jaiwal, P. K. (2007) *Agrobacterium tumefaciens* mediated transfer of *Phaseolus vulgaris*; *V. unguiculata* α-amylase inhibitor-1 gene into mungbean *Vigna* radiate (L.) Wilezek using bar as selectable marker (2007) Plant Cell Report 26:187-198, in cowpea seeds (*Vigna unguiculata*) (Solleti, S. K., Bakshi, S., Purkayastha, J., Panda, S. K., Shoo, L. Transgenic cowpea (*Vigna unguiculata*) seeds expressing a bean α-amylase inhibitor 1 confer resistance to storage pests, bruchid beetles. Plant Cell Report 27: 1841-1850. 2008.

The use of genes coding for these kinds of proteins and the expression thereof in heterologous systems (transgenic plants) surmounts the difficulties caused by the use of bioinsecticides or chemical insecticides. However, so far there is only one account of the use of protein inhibitor in the production of transgenic cotton for controlling insect (cpti— which encodes for a trypsin and chymotrypsin inhibitor, utilized by the public sector in China (Shirong, J In Transgenic Cotton—Chapter 7—Bt/CpTI Insect Resistant Cotton, Science Press Beijing/New York, 2004).

Currently, the transgenic plants expressing isolated-type αAIs common bean genes belong in the Leguminosae family (bean, pea, chick pea) and *Coffea arabica* plant (Rubiaceae family). Thus, no invention has described a gene of that nature with potential application to cotton plants (Malvaceae family) so far. In the present invention there is a combinatorial library which applies the DNA Shuffling technique (Stemmer, W. P. C., 1994 Rapid evolution of a protein in vitro by DNA shuffling. Lett. Nat. 370, 389-391; Zhao, H., Arnold, F. H., 1997 Opmitization for DNA shuffling for high fidelity recombination. Nucleic Acids Res. 25, 1307-1308) aiming at developing analogous mutant genes which also encode for alpha-amylase inhibiting proteins.

The DNA Shuffling consists in a directed molecular evolution, which causes significant changes in the primary structure of the DNA molecules by means of random mutations (Ling Yuan, L. Kurek, I., English, J. and Keenan, R. Laboratory-directed protein evolution. Microbiology and Molecular Biology Reviews, Vol. 69, No. 3, p. 373-392, 2005; Stemmer, W. P. C. Rapid evolution of a protein in vitro By Embaralhamento de ADN. Nature. London, Vol. 370, p. 389-391, 1994, U.S. Pat. Nos. 5,605,793, 5,811,238, 5,830, 721). The genes of interest are first randomly fragmented into small sequences of 50-300 pairs of base, and said product is recombined in a PCR (Polymerase Chain Reaction), which is carried out with no addition of oligonucleotides. In a second consecutive reaction the products of the first reaction and specific oligonucleotides are added. Thus it allows for the amplification of a population of analogous mutant/variant genes (Stemmer, W. P. C. Rapid evolution of a protein in vitro by Embaralhamento de ADN. Nature. London, Vol. 370, p. 389-391, 1994; Zhao, H. and Arnold, F. H. Functional and nonfunctional mutations distinguished by random recombination of homologous genes. Proc. Natl. Acad. Sci. U.S.A., Vol. 94, p. 7997-8000, 1997).

The effectiveness of the art to produce analogous molecules with improved biological activity can be found in several works, such as for instance, in Jager et al (Jager, S. A. W., Jekel, P. A. and Janssen, D. B. Hybrid penicillin acylases with improved properties for synthesis of β-lactam antibiotics. Enzyme And Microbial Technology, Vol. 40, p. 1335-1344, 2007), wherein the enzymatic activity of the penicillin acyclase increased 90%. The art may utilize one or more homologous genes and its success depends on a delicate arrangement involving the library size, the biological diversity derived therefrom and a methodology for selecting the variants with the desired characteristic (Ling Yuan, L. Kurek, I., English, J. and Keenan, R. Laboratory-directed protein evolution. Microbiology and Molecular Biology Reviews, Vol. 69, No. 3, p. 373-392, 2005).

Thus, the present invention aims at solving the problem regarding the abusive use of chemical insecticides as well as increasing the plants resistance, generating transgenic plants which are capable of expressing genes that encode for molecules having improved alpha-amylase inhibiting activity.

SUMMARY OF THE INVENTION

The present invention relates to the field of insect pests control, using methods and compositions which comprise mutant analogues of alpha-amylase inhibitors (αAIs).

More specifically, the present invention relates to isolated nucleic acid molecules characterized by comprising:

a) sequences substantially similar to any of the sequences selected from the group identified as SEQ ID NOs: 1-3;

b) complements to the sequences described in SEQ ID NOs: 1-3;

c) reverse complements to the sequences described in SEQ ID NOs: 1-3;

d) reverse sequences of the sequences described in SEQ ID NOs: 1-3.

A second embodiment of the present invention relates to a gene construct containing the isolated nucleic acid molecule.

A third embodiment of the present invention relates to a binary vector characterized by containing a gene construct. More specifically the present invention relates to a binary vector characterized by comprising:

a. a promoter optionally linked to a leader sequence and operationally linked to b. an encoding sequence substantially similar to any of the sequences identified as SEQ ID NO1-2 operationally linked to;

c. a termination signal;

d. a replication origin;

e. a selection marker; and f. a cloning site

A fourth embodiment of the present invention relates to isolated polypeptides, characterized by comprising sequences substantially similar to any of the sequences selected from the group identified as SEQ ID NOs: 4-6.

A fifth embodiment of the present invention relates to a transformed cell characterized by containing a gene construct or a binary vector containing the nucleic acid molecules of the present invention; or a polypeptide of the present invention.

A sixth embodiment of the present invention relates to a plant or part thereof, or a propagule or progeny thereof characterized by comprising a gene construct or a binary vector containing the nucleic acid molecules of the present invention; or a polypeptide of the present invention.

A seventh embodiment of the present invention relates to a plant or part thereof, or a propagule or progeny thereof characterized by comprising a gene construct or a binary vector containing the nucleic acid molecules of the present invention; or a polypeptide of the present invention.

An eighth embodiment of the invention relates to a method for producing a genetically modified organism characterized by comprising the following steps:

a. transforming a cell, tissue, organ or embryo with a gene construct or a binary vector containing the nucleic acid molecules of the present invention;

b. selecting transformed cells, callus cells, embryos or seeds;

c. regenerating mature plants, mature embryos or transformed cell microorganisms, callus cells, embryos or seeds selected in step (b);

d. selecting mature plants, mature embryos or cells of microorganisms from step (c) containing the gene construct or binary vector containing the nucleic acid molecules of the present invention.

A ninth embodiment of the present invention relates to a method for producing recombinant protein characterized by comprising the following steps:

a. transforming a cell, tissue, organ or embryo with a binary vector containing the nucleic acid molecules of the present invention;

b. selecting transformed cells, callus cells, embryos or seeds;

c. regenerating mature plants, mature embryos or transformed cell microorganisms, callus cells, embryos or seeds selected in step (b);

d. selecting mature plants, mature embryos or cells of microorganisms from step (c) containing binary vector containing the nucleic acid molecules of the present invention;

e. extracting the recombinant protein produced by the organisms selected from step (d).

A tenth embodiment of the present invention relates to a recombinant protein obtained by the method described in claim 37.

An eleventh embodiment of the present invention relates to a biodegradable pesticidal composition characterized by comprising an effective concentration of the isolated polypeptide according to any of claims 21-25 or an analogous mutant, in an agronomically acceptable carrier.

A twelfth embodiment of the present invention relates to a method for controlling a pest characterized by comprising the following steps: a) detecting the occurrence of the pest in an environment;

b) promoting the contact of the pest with an isolated pesticidal protein or with a composition of the invention, wherein said protein consists of the sequences selected from a group of amino acid sequences described in SEQ ID NOs: 4-6.

A thirteenth embodiment of the present invention relates to a method of production of transgenic lines resistant to an insect pest, characterized by comprising the following steps:

a) transforming a cultivar of interest with a gene construct or a binary vector containing the nucleic acid molecules of the present invention;

b) regenerating transgenic lines containing said construct stably integrated into their genomes;

c) selecting the transgenic lines having the highest levels of expression of the alpha-amylase inhibitor of the invention.

DETAILED DESCRIPTION OF THE INVENTION

Figure 1:
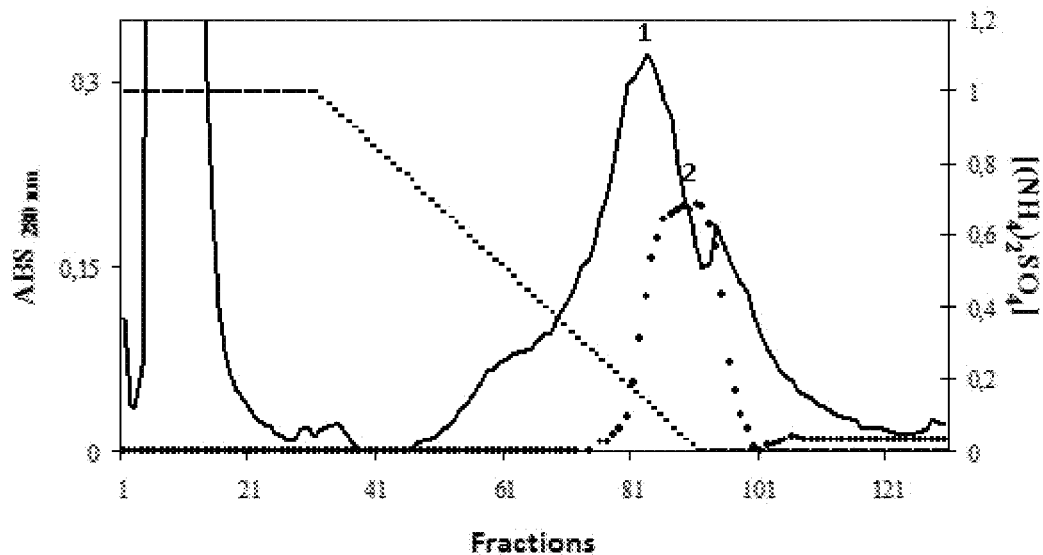
FIG. 1. Chart displaying the chromatographic profile of the purification of α-amylases proteins extracted from the bowels of *A. grandis* larvae, using ion-exchange resin. Decreasing linear gradient sulfate (----), Absorbance at 280 nm (_____) Fractions showing the activity of α-amilases (2).

The invention describes new alpha-amylase inhibitors and methods, which allow for the generation of technologies capable of controlling insect pests of great economic interest. More specifically, the nucleic acids (genes) of the present invention, including fragments and variants thereof, comprise nucleotide sequences substantially similar to the sequences identified as SEQ ID NOs: 1-3, which encode for inhibitory proteins substantially similar to the sequences identified as SEQ ID NOs: 4-6 containing mass of approximately 24 kDa, processed into two sub-units α and β (15 kDa and 9 kDa). The inhibitory proteins described are preferably biologically active against the Coleopteran insect pest: boll weevil, *Anthonomus grandis.*

The invention involves a strategy to help control the pest, comprising the steps of producing and selecting new genes to be inserted into plants via genetic modification, in order to make them resistant to said pest. The production involves recombining and generating new molecules and relates to the product from the application of the DNA shuffling technique. The selection is related to the application of the Phage display technique—it results in choosing genes according to a desired characteristic. The techniques employed in producing and selecting new genes are already well described in the art.

Besides the nucleotide sequences, the present invention also describes a gene construct and a binary vector comprising the gene sequences encoding for proteins having improved inhibitory activity (ATCC filing number: PTA-11584 for the protein sequence of SEQ ID NO: 3; PTA-11585 for the protein sequence of SEQ ID NO: 2; and PTA-11586 for the protein sequence of SEQ ID NO: 1). The binary vector is further characterized by comprising:

a. a promoter optionally linked to a leader sequence and operationally linked to b. an encoding sequence substantially similar to any of the sequences identified as SEQ ID NOs: 1-3 operationally linked to;

c. a termination signal;

d. a replication origin;

e. a selection marker; and f. a cloning site.

The present invention also provides a cell, plant, microorganisms containing the nucleic acid molecules and/or peptide of the present invention.

The present invention provides new techniques, which do not depend upon the use of the traditional synthetic chemical pesticides. The invention relates to natural biodegradable pesticides and genes coding them.

The invention provides the creation of genes analoguous to αAI-1 and αAI-2, isolated from beans. Analogous mutant genes—also encoding for alpha-amylase inhibitors—have been created by means of in vitro mutation.

The invention also relates to a method for producing an organism genetically modified characterized by comprising the following steps:

a. transforming a cell, tissue, organ or embryo with a gene construct or a binary vector containing the nucleic acid molecules of the present invention;

b. selecting transformed cells, callus cells, embryos or seeds;

c. regenerating mature plants, mature embryos or transformed cell microorganisms, callus cells, embryos or seeds selected in step (b);

d. selecting mature plants, mature embryos or cells of microorganisms from step (c) containing the gene construct or binary vector containing the nucleic acid molecules of the present invention.

The present invention further relates to a method for producing recombinant protein characterized by comprising the following steps:

a. transforming a cell, tissue, organ or embryo with a binary vector containing the nucleic acid molecules of the present invention;

b. selecting transformed cells, callus cells, embryos or seeds;

c. regenerating mature plants, mature embryos or transformed cell microorganisms, callus cells, embryos or seeds selected in step (b);

d. selecting mature plants, mature embryos or cells of microorganisms from step (c) containing the binary vector containing the nucleic acid molecules of the present invention;

e. Extracting the recombinant protein produced by the organisms selected from step (d).

The present invention relates also to a biodegradable pesticidal composition characterized by comprising an effective concentration of the isolated polypeptide of the present invention 25 or an analogous mutant, in an agronomically acceptable carrier.

The invention relates to a method for controlling a pest characterized by comprising the following steps:

a) detecting the occurrence of the pest in an environment;

b) promoting the contact of the pest with an isolated pesticidal protein or with a composition of the invention, wherein said protein consists of the sequences selected from a group of amino acid sequences described in SEQ ID NOs: 4-6.

The present invention also relates to a method of production of transgenic lines resistant to an insect pest, characterized by comprising the following steps:

a) transforming a cultivar of interest with a gene construct or a binary vector containing the nucleic acid molecules of the present invention;

b) regenerating transgenic lines containing said construct stably integrated into their genomes;

c) selecting the transgenic lines having the highest levels of expression of the alpha-amylase inhibitor of the invention.

For the construction of the DNA library of the present invention the alpha-amylase inhibitors, called αAI-1 and αAI-2, have been recombined. The products of the original genes have specific activities towards the amylases of some bruchid insects, but to not inhibit the alpha-amylase of boll weevil. However, the analogous mutant genes created, when expressed and proteolytically processed into model plants have a different in vitro effect with regard to the inhibition of the alpha-amylases of boll weevil.

In order to obtain the αAIs analogous genes, for inhibotors highly active against alpha-amylases of boll weevil, genes αAI-1 and αAI-2, isolated from common bean (*P. vulgaris*), have been employed. Both genes have been mixed and used as substrate in order to produce variant genes by means of the DNA Shuffling technique. The variants have been selected in view of their capability to bond with isolated alpha-amylase enzymes from the bowel of insects and larvae of boll weevil, by presenting proteins on the surface of Phage display bacteriophages (Barbas III, C. F.; Burton, D. R.; Scott, J. K.; Silverman, G. J. Selection from antibody libraries. In: *Phage display*—A laboratory manual—USA: Cold Spring Laboratory, p. 10.1-10.20, 2001).

The construction of analogous variant gene libraries, using in vitro molecular evolution techniques, has been employed for the last three decades. This is due to the advent of biotechnological tools which serve as a genetic engineering platform for the development of new molecules having improved activity, aiming mainly for agriculture and pharmaceutical industry fields (Ling Yuan, L. Kurek, I., English, J. and Keenan, R. Laboratory-directed protein evolution. Microbiology and Molecular Biology Review. Vol. 69, No. 3, p. 373-392, 2005). Several techniques—including chemical modifications, error-prone PCR and site-directed mutagenesis—can be used in order to create mutations in a gene sequence (Neylon, C. Chemical and biochemical strategies fot the randomization of protein encoding DNA sequences: library construction methods for directed evolution. Nucleic Acids Research, vol. 32, N. 4, PP. 1448-1459, 2004). Preferably in the present invention major importance is givent to the DNA Shuffling technique (Rosic, N. N., Huang, W., Johnston, W. A., James J. Devoss, J. J., Gillam, E. M. J. Extending the diversity of cytochrome P450 enzymes by ADN family shuffling. Gene, Vol. 35762, No of Pages 9, 2007; Ling Yuan, L. Kurek, I., English, J. and Keenan, R. Laboratory-directed protein evolution. Microbiology and Molecular Biology Reviews, Vol. 69, No. 3, p. 373-392, 2005; Abécassis, V., Pompon, D. and Truan, G. High efficiency family shuffling based on multi-step PCR and in vivo ADN recombination in yeast: statistical analysis of a combinatorial library between human cytochrome P450 1A1 and 1A2. Nucleic Acids Research, Vol. 28, No. 20: E 88, 2000; Zhao, H. and Arnold, F. H. Functional and nonfunctional mutations distinguished by random recombination of homologous genes. Proc. Natl. Acad. Sci. U.S.A., Vol. 94, p. 7997-8000, 1997; Stemmer, W. P. C. Rapid evolution of a protein in vitro By Embaralhamento de ADN. Nature. London, Vol. 370, p. 389-391, 1994). The DNA Shuffling strategy disclosed by the present invention has the advantage of generating at the same time a wide diversity of mutants containing randomly produced mutations.

For the selection of αAIs gene variants in the present invention the technique consisiting in the presentation of proteins on the surface of Phage Display bacteriophages was used (Zhang, Q., Bai, G., Cheng, J., Yu, Y., Tian, W. and Yang, W. Use of an enhanced green fluorescence protein linked to a single chain fragment variable antibody to localize *Bursaphelenchus xylophilus* cellulose. Biosci. Biotechnol. Biochem, Vol. 71, No 6, p. 1514-1520, 2007; Andris-Widhopf, J., Rader, C., Steinberger, P., Fuller, R., Barbas III, C. F. Methods for the generation of chicken monoclonal antibody fragments by Phage display. Journal of Immunological Methods, Vol. 242, p. 159-181, 2000; Stoop, A. A., Jespers, L., Lasters, I., Eldering, E. and Pannekoek, H. High-density mutagenesis by combined Embaralhamento de ADN and Phage display to assign essential amino acid residues in protein-protein interactions: application to study structure-function of plasminogen activation inhibitor 1 (PAI-1). J. Mol. Biol., Vol. 301, p. 1135-1147, 2000; Barbas III, C. F., Bain, J. D., Hoekstra, D. M., And Lerner, R. A. Semisynthetic combinatorial antibody libraries: A chemical solution to the diversity problem. Proc. Nati. Acad. Sci. USA, Vol. 89, p. 4457-4461, 1992). The association of DNA Shuffling techniques with the presentation of proteins on the surface of Phage Display bacteriophages (creation of combinatorial libraries) makes the selection and expression of new molecules much more efficient (Stoop, A. A., Jespers, L., Lasters, I., Eldering, E. And Pannekoek, H. High-density mutagenesis by combined Embaralhamento de ADN and Phage display to assign essential amino acid residues in protein-protein interactions: application to study structure-function of plasminogen activation inhibitor 1 (PAI-1). J. Mol. Biol., Vol. 301, p. 1135-1147, 2000).

In the end, the enzymatic inhibition effect of the original inhibitors αAI-1 and αAI-2 and their analogous mutants has been assessed in vitro by utilizing protein extracts from model plants transformed with said genes. Thus, the original and the selected analogous genes have been subcloned into binary vector for expression in plants and the recombinant proteins created utilized in in vitro assays against the main pest to attack the cotton plant: boll weevil.

In the following description, several different terms are exhaustively used. The following definitions are provided so as to make the comprehension of the invention easier.

The term "isolated nucleic acid molecule" is employed to relate to the nucleic acids of the present invention. Said term, when related to the DNA of the present invention, is relative to the DNA molecule originated from the recombination of two DNA molecules (αAI-1 and αAI-2). For instance, the "isolated nucleic acid molecule" can be inserted into a vector, such as viral vector or plasmid, or integrated with a gene DNA of a prokaryote or eukaryote. An "isolated nucleic acid molecule" may also comprise a cDNA molecule. An isolated nucleic acid molecule inserted into a vector is also herein referred to as a recombinant nucleic acid molecule. The term "isolated nucleic acid molecule" may also refer to RNA molecules transcribed from a DNA molecule as described above.

The definition of the terms "complement", "reverse complement" and "reverse sequence" as employed herein is illustrated by the following example: the complement to sequence 5'AGTGAAGT3' is 3'TCACTTCAS', its reverse complement is 3'ACTTCACTS' and its reverse sequence is 5'TGAAGTGA3'.

As employed herein, "variant" or "substantially similar" or even "analogous peptide" or "analogous mutant" comprises amino acid or nucleotide sequences different from specifically identified sequences, wherein one or more nucleotides or amino acid residues is deleted, substituted or added and may have its biological activity altered, aided, increased or reduced when compared to the native or non-mutated parental protein. The variants can be naturally-occurring allelic variants or non-naturally occurring variants. The variant or substantially similar sequences are relative to fragments of nucleic acids or peptides which can be characterized by the identity percentage of their sequences if nucleotides or amino acids with the nucleotide sequences (SEQ ID NOs: 1-3) or amino acid sequences (SEQ ID NOs: 4-6) described herein, as determined by common algorithms employed in the art. The preferred fragments of nucleic acids or peptides are those which nucleotide sequences or amino acid sequences have at least about 40 or 45% sequence identity, preferably about 50% or 55% sequence identity, more preferably about 60% or 65% sequence identity, more preferably about 70% or 75% sequence identity, more preferably about 80% or 85% sequence identity, even more preferably about 90%, 91%, 92%, 93%, 94%, 95%, 96%, 97%, 98% or 99% sequence identity when compared to the reference sequence. The percentage identity is determined by the alignment of two sequences to be compared, determining the number of identical residues in the aligned portion, dividing the number obtained by the total number of residues in the researched sequence and multiplying the result by 100. Said alignment can be performed through public domain tools, such as BLASTN and BLASTP, available on NCBI website (http://www.ncbi.nlm.nih.gov). The sequence alignment and the identity percentage calculation of the present invention have been performed as per the sequences filed with the GenBank. The term "analogous synthetic" as cited herein relates to the modification of the nucleotide sequences of the variants selected. Modifications to nucleotide base substitutions appropriating to the preferred base codon, inherent in the plant utilized in the genetic transformation. The new sequence is obtained by means of chemical synthesis, and the nucleotide substitutions do not represent alteration in the translated amino acid sequence.

"Encoding sequence" relates to the DNA sequence which encoded for a specific protein and excludes the non-encoding sequence. An "interrupted encoding sequence" means a separating sequence (for instance, one or more introns joined together by junctions). An "intron" is a nucleotide sequence transcribed and present in pre-mRNA, but removed by means of cleavage and rebonding of the mRNA within the cell generating a mature mRNA which can be translated into a protein. Examples of introns include, but are not limited to, pdk2 intron, catalase intron from castor oil plant, Delta 12 desnaturase intron from cotton, Delta 12 desnaturase from *Arabidopsis*, maize ubiquitin intron, SV40 intron, malate synthase gene intron.

A "gene construct" is a gene comprising a promoter and a coding region of different origins. In the present case, the gene construct comprises the polynucleotides of the present invention associatedly or isolatedly linked to the regions which regulate expression, such as promoters and termination signals.

Gene constructs comprising promoters linked to nucleic acids is known in the art and can be found in Sambrook, et al. (Molecular Cloning, A Laboratory Manual, 2nd ed. (1989), Cold Spring Harbor Laboratory Press).

The term "vector" relates to a replicon, like a plasmid, phague or virus, with which other genetic sequences or elements (either ADN or RNA) can be bonded. Thus, the genes can be replicated together with the vector. Preferably one of the vectors of interest of the present invention is relative to the phagemid. "Phagemid" relates to a vector which contains sequence for replication into phage and bacterium, said vector having characteristics that meet the specifications of the host cell as well as selecting agents and promoters. An example includes the phagemid pComb3X (Andris-Widhopf, J.; Rader, C.; Steinberger, P.; Fuller, R., Barbas III, C. F. Methods for the generation of chicken monoclonal antibody fragments by Phage display. Journal of Immunological Methods, 242: 159-181, 2000), which characteristic consists in fusing the gene of interest to the gene of protein III, of the filamentous bacteriophage M13, located at the viral capsid. "Recombinant vector" results from the combination of a commercial vector with genes of the present invention operationally linked to an endogenous and/or heterologous polynucleotide of interest which, in turn, is operationally linked with a termination signal. Such vectors can be found on the market, including Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). Some examples of vectors utilized in the present invention include, nut are not limited to, pGEM-T easy (Promega Corporation), pCambia 2300 (Canberra, Australia), pComb3X (Andris-Widhopf, J.; Rader, C.; Steinberger, P.; Fuller, R., Barbas III, C. F. Methods for the generation of chicken monoclonal antibody fragments by Phage display. Journal of Immunological Methods, 242: 159-181, 2000). Gene constructs comprising promoters linked to nucleic acids is known in the art and can be found in Sambrook, et al. (Sambrook, J., Russell, D. W., Molecular Cloning, A Laboratory Manual, 2nd ed., Cold Spring Harbor Laboratory Press. 1989).

A "binary vector" is a vector derived from plasmids capable of replicating both into *Escherichia coli* and *Agrobacterium*. For the present invention the following binary vectors have been preferably utilized: pFSp12300AIC3 (ATCC number PTA11586, containing the nucleotide sequence of SEQ ID NO: 1), pFSp12300AIG4 (ATCC number PTA11584, containing the nucleotide sequence of SEQ ID NO: 3) and pFSp12300AIA11 (ATCC number PTA11585, containing the nucleotide sequence of SEQ ID NO: 2). A plant transformation vector based on the *Agrobacterium* binary system must contain an appropriate origin of replication and a gene for selection in bacterium, usually antibiotic resistance. Furthermore, it should preferably contain a multiple cloning site region (containing sequences of restriction enzymes) between the ends of the T-DNA for insertion of the desired gene sequences, and a transfer region (ori I) and activation site for conjugation. Once the binary vector is obtained with the desired gene sequence—operationally linked—it must be transferred to *Agrobacterium*. Such vectors can be found on the market, including Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.) and Promega (Madison, Wis.) or obtained through public donation (pCambia series, Canberra, Australia). "Operationally linked" means that the regulatory sequences necessary for the expression of the coding sequence are placed into the DNA molecule at appropriate positions in relation to the coding sequence to effect its expression. Said definition is sometimes applied to the arrangement of coding sequences and transcription-controlling elements (for instance, promoters or enhancers and termination elements) in the binary vector. An exogenous coding region is typically bordered by operationally linked regulatory regions which regulate the expression of the exogenous coding region in a transformed cell (either a plant or animal microorganism). A typical regulatory region operationally linked to an exogenous coding region includes a promoter, i.e., a fragment of nucleic acid which may lead to transcription of exogenous coding regions, positioned at 5' region of the exogenous coding region.

"Operationally linked" means that the regulatory sequences necessary for the expression of the coding sequence are placed into the DNA molecule at appropriate positions in relation to the coding sequence to effect its expression. Said definition is sometimes applied to the arrangement of coding sequences and transcription-controlling elements (for instance, promoters or enhancers and termination elements) in the binary vector. An exogenous coding region is typically bordered by operationally linked regulatory regions which regulate the expression of the exogenous coding region in a transformed cell (either a plant or animal microorganism). A typical regulatory region operationally linked to an exogenous coding region includes a promoter, i.e., a fragment of nucleic acid which may lead to transcription of exogenous coding regions, positioned at 5' region of the exogenous coding region. The present invention is not limited to the use of any particular promoter; a wide array of promoters is known in the art. Promoters can be, but are not limited to, inducible-, constitutive- and tissue-specific-type. Preferably, the promoter of the present invention is selected from the group of the cotton fiber gene promoters, and can be, but is not limited to, E6, H6S, Rac13, LTP, ACP, Expansin, CAP, Annexin, FbL2A and actin 2.

In one of the aspects of the invention, the promoter is a constitutive promoter. In another aspect of the invention, the promoter activity is stimulated by external or internal factors such as, but not limited to, hormones, chemical compounds, mechanical impulses and biotic or abiotic stress conditions. The promoter activity may also be regulated on a time and space basis (e.g., tissue-specific promoters and promoters regulated during development).

The promoter may contain enhancers. An enhancer is a DNA sequence that can stimulate the promoter activity. It may either be an inherent element in the promoter or a heterologous element inserted in order to increase the level and/or the tissue-specificity of a promoter. "Constitutive promoters" are those that direct the gene expression in all the tissues all the time. "Tissue-specific" promoters or "development-specific" promoters are those that direct the gene expression virtually exclusively in specific tissues, such as leaves, roots, stems, flowers, fruits or seeds, or in specific development stages of a tissue, as in the beginning or in the end of the embryogenesis.

In one of the aspects of the invention, the promoter is a plant-expressed promoter. As employed herein, "plant-expressed promoter" means a DNA sequence capable of starting and/or controlling transcription in a plant cell. It includes any plant-derived promoter; any non-plant-derived promoter capable of directing the synthesis of the gene present in the T-DNA of *Agrobaterium*; tissue-specific or organ-specific promoters, including—but no tlimited to—seed-specific promoters (WO8903887), organ primordial specific promoters (as mentioned by patent application US20030175783, An, Y. Q., Huang, S., McDowell, J. M., McKinney, E. C., Meagher, R. B., Conserved expression of the *Arabidopsis* ACT1 and ACT3 actin subclass in organ primordia and mature pollen. The Plant Cell 8, 15-30, 1996), stem-specific promoters (as mentioned by patent application US20030175783, Keller, B., Sauer, N., Lamb, C. J., Glycine-rich cell wall proteins in bean: Gene structure and association of the protein with the vascular system. EMBO J. 7: 3625-3633, 1988), leaf-specific promoters (as mentioned by patent application US20030175783, Hudspeth, R. L., Grula, J. W., Structure and expression of the maize gene encoding the phosphoenolpyruvate carboxylase involved in C4 photosynthesis. Plant Mol Biol 12:579-589, 1989), mesophile-specific promoters, root-specific promoters (as mentioned by patent application US20030175783, Keller, B., Lamb, C. J., Specific expression of a novel cell wall hydroxyproline-rich glycoprotein gene in lateral root initiation. Genes Devel. 3:1639-1646, 1989), tuber-specific promoters (as mentioned by patent application US20030175783, Keil, M., Sánchez-Serrano, J. J., Willmitzer, L., Both wound-inducible and tuber-specific expression are mediated by the promoter of a single member of the potato proteinase inhibitor II gene family. EMBO J. 8: 1323:1330, 1989), vascular tissue-specific promoters (as mentioned by patent application US20030175783, Peleman J., Saito, K., Cottyn, B., Engler, G., Seurinck, J., Van Montagu, M., Inze, D., Structure and expression analyses of the S-adenosylmethionine synthetase gene family in *Arabidopsis thaliana*. Gene 84: 359-369, 1989), stamen-specific promoters (WO8910396, WO9213956), dehiscence zone-specific promoters (WO9713865); and the like. Preferably, the invention includes cotton fiber gene promoters, which include, but are not limited to, E6, H6S, Rac13, LTP, ACP, expansin, CAP, annexin, FbL2A and actin actina 2 gene promoters.

As employed herein, "bacterium-expressed promoter" means a DNA sequence capable of starting and/or controlling transcription in a bacterial cell. As employed herein, "fungus-expressed promoter" means a DNA sequence capable of starting and/or controlling transcription in a fungal cell. As employed herein, "insect-expressed promoter" means a DNA sequence capable of starting and/or controlling transcription in an insect cell.

A "leader sequence" or "signal sequence" in the present invention means a nucleic acid sequence that—when operationally linked to a nucleic acid molecule—allows for the secretion of the product of the nucleic acid molecule. The leader sequence is preferably located at the 5' region of the nucleic acid molecule. Preferably, the leader sequence is obtained from the same gene as that of the promoter used for directing the transcription of the nucleic acid molecule, or from the gene from where the nucleic acid molecule derives. The present invention preferably makes use of the signal sequence derived from a Brazilian cotton cultivar.

The termination signal of the transcription and the polyadenylation region of the present invention include, but are not limited to, SV40 termination signal, HSV TK adenylation signal, nopaline synthethase gene termination signal of *Agrobacterium tumefasciens* (NOS), octopine synthethase gene termination signal, 19S and 35S gene termination signal of CaMV, gene termination signal of maize alcohol dehydrogenase, mannopine synthethase gene termination signal, beta-phaseolin gene termination signal, ssRUBISCO gene termination signal, sucrose synthetase gene termination signal, termination signal of the virus which attacks *Trifolium subterranean* (SCSV), trpC gene termination signal of *Aspergillus nidulans* and the like.

As previously described, "binary vectors" can comprise an inducible promoter operationally linked to a nucleic acid sequence coding for the insecticidal protein of the present invention. "Inducible" promoters can direct the expression of a polynucleotide with which they are operationally linked, in a tissue or specific development stage or responding to environment conditions. In one of the aspects of the invention, expression vectors comprise a firmly regulated inducible promoter operationally linked to a nucleic acid molecule coding for an insecticidal protein. Said binary vector can further comprise a selectable marker (e.g., a gene coding for a protein which confers antibiotic resistance) operationally linked to a constitutive promoter or with a firmly regulated inducible promoter. Depending on the application, it can benefit the expression of the nucleic acid sequence coding for an insecticidal protein by means of an insect pest inducible promoter. In one aspect of the present invention, utilizing promoters which are expressed locally or close to the pest infection site may be advantageous.

"Selection marker" is herein referred to as sequences conferring antibiotic resistance or as visual markers. Preferably, the markers can be selected from—but not limited to, the group of sequences encoding for the following genes: kanamycin, neomycin, amplicilin, chloramphenicol, streptomycin, hygromycin, geneticin, phosphinothricin, glyphosate, glufosinate ammonium, AHAS, BAR and GUS. Organisms (plants or bacteria) which survive the selectable marker (or resistance gene) in a culture medium or in topical applications are indicated as positive transformants characterized by the presence of exogenous gene integrated with the genome of said organism.

The term "oligonucleotide" is herein referred to as primers and 'probes' of the present invention and defined as a nucleic acid molecule comprising from ten to ninety deoxyribonucleotides, preferably more than eight. The exact size of the oligonucleotides depends on the experimental factors specific to each step of the process.

As employed herein, the terms "coding", "encoding" or "encoded" when employed in the context of a specific nucleotide sequence means that said sequence has an information, which will be biologically translated from the nucleotide sequence into a specific protein sequence. The information with which a protein is encoded is specified by the use of codons. Said codons are explored by each living organism in different ways and different portions of nucleotide sequences may be biologically translated into identical codons.

The term "gene" corresponds to a specific nucleotide sequence located at a particular region of the chromosome and is responsible for encoding a specific final product. The gene also has in its primary structure all the necessary information for the processes of biological transcription and translation, such as, transcription promoting and regulating regions. In the present case, gene comprises the coding nucleotide sequences corresponding to the inhibitors ($\alpha$AIs) from *P. vulgaris* and to the analogous gene thereof.

The terms "polypeptide", "peptide" and "protein" are used in an inter-related way to refer to an amino acid residue polymer. The terms apply to amino acid polymers wherein one or more amino acid residue is an artificial chemical analog of a corresponding naturally-occurring amino acid, as well as to naturally-occurring amino acid polymers.

The polypeptides of the invention can be produced either by a nucleic acid herein described or by using standard molecular Biology techniques. For instance, a truncated protein of the invention can be produced by the expression of a recombinant nucleic acid of the invention in an appropriate host cell, or alternatively by the combination of procedures, such as digestion utilizing protease and purification.

In the present invention the isolated polypeptides are characterized by comprising sequences substantially similar to any of the sequences selected from the group identified as SEQ ID NOs: 4-6 and exhibiting insecticidal activity when orally administered to susceptible insect larvae. The polypeptides of the present invention are characterized by exhibiting insecticidal activity when provided on a diet orally administered to the larva of a coleopteran insect, more specifically to the boll weevil larva. More specifically, the isolated polypeptides of the present invention are characterized by being an $\alpha$-amylase inhibitor.

In the present invention the term "recombinant protein" relates to the chimeric molecules resulting from the application of the gene's DNA Shuffling technique (encoding alpha-amylase inhibitors). Said molecules can be expressed in, but not limited to, phages, bacteria, yeasts and plants. Preferably, the recombinant protein of the present invention is characterized by inhibiting alpha-amylase.

The term "substantially pure" relates to preparations comprising at least 50-60 weight % of the component of interest (for instance, nucleic acid, oligonucleotide, polypeptide, protein etc). Preferably, the preparation comprises at least 75 weight %, and more preferably 90-99 weight % of the component of interest. Purity is measured by means of methods appropriate for the component of interest (for instance, mass spectrometry and the like).

"Isolated gene" is also utilized in the present invention. Said term relates to the nucleotide sequence existing in a certain genome, specifically of common beans *P. vulgaris* which codes for a protein.

The term "isolated protein" or "isolated and purified protein" is sometimes employed in the present invention.

Said term relates to a protein produced by the expression of an isolated nucleic acid molecule of the present invention. Alternatively, said term may relate to a protein that has been sufficiently separated from other proteins which it could be naturally associated with, such as it is in its "substantially pure" form. The term "isolated" does not exclude synthetic or artificial mixtures with other compounds or materials, or the presence of impurities which do not interfere with the fundamental activity of the protein, and that may be present, for instance, in an incomplete purification, addition of stabilizers, or combined within, for example, in an agriculturally acceptable composition.

The term "biological activity" is relative to a function or a group of functions performed by a molecule in a biological context (i.e., in an in vitro organism or its substitute or any other similar model). The biological activity of the proteins which are digestive enzyme inhibitors is characterized by the post-translational proteolytic processing and by the physicochemical properties such as, e.g., the presence of residues that form the active site, causing affinity (bonding or accommodation with specific enzymes). Said affinity with molecules can be produced by the mere chemical interaction between both of them.

As employed herein, the term "impacting on insect pests" relates to the effect of changing the diet, growth, and/or behavior of insects in any stage of development, including, but not limited to: killing the insects; delaying their growth; ceasing their reproductive capacity; antifeeding activity; and the like.

"Pesticidal activity" and "insecticidal activity" are used synonymously to refer to the activity of an organism or substance (e.g.: a protein) which can be measured by, but not limited to, the mortality of the pest, weight loss of the pest, pest repellency and other behavior and physical changes of a pest after feeding and exposition for an appropriate period of time. Thus, the impact of the pesticidal activity must have at least one measurable pest fitness parameter. For instance, "pesticidal and/or insecticidal proteins" are proteins which start the pesticidal activity themselves or together with other proteins. Alpha-amylase inhibitors are pesticidal proteins. Other examples include, for example, 1-pentyne and jaburetox 8-endotoxins.

The term "effective amount of pesticide" relates to the amount of a substance or organism exhibiting pesticidal activity when present in the environment where the pest lives. For each substance or organism, the effective amount of pesticide is empirically determined according to each affected pest in a specific environment. Similarly, "effective amount of pesticide" can be used to refer to an "effective amount of pesticide" when the pest is an insect pest. The term "biodegradable pesticidal composition" is characterized by being products or substances applied to the soil for action in the environment where the pest lives that can be degraded by—but not limited to—microorganisms, photolysis, oxidation in a short period of time. The biodegradable compositions comprise substances classified as organophosphorus compounds, carbamates, triazines, anilines, and can be stuck into the soil like stakes without causing permanent damage. The products generally comprise a solid, hydrophilic, water-soluble polymeric binder, and a systemic pesticide. Moreover, the biodegradable pesticide is characterized by the fact that an acceptable carrier may be a surface-active agent, an inert carrier, a preservative, a humectant, a feeding stimulant, an attractant, an encapsulating agent, a binder, an emulsifier, a colorant, an UV (ultraviolet) shield, a buffer, a flow agent or fertilizer, micronutrient donors, or other preparations which influence plant growth. The biodegradable pesticidal composition is characterized by the fact that the acceptable carrier is a transformed microorganism. In the present invention, the biodegradable pesticidal composition is characterized by the fact that the polypeptide or analogous mutant is used in combination with Bt δ-endotoxins or other insecticidal proteins.

The term "recombinantly engineered" or "engineered" relates to the use of the recombinant DNA technology to generate (to engineer) a change in the structure of the protein based on the understanding of the action mechanism thereof, and the amino acids may be introduced, deleted or substituted.

The term "DNA shuffling" is used to describe a method used in in vitro directed molecular evolution to generate variants of a sole gene sequence, or two or more homologous gene sequences through the recombination of fragments randomly generated with recovery of modified sequences and with consequent modification of amino acid residues in the encoding protein by the mutant analogous.

The term "presentation of proteins in the bacteriophage surface—Phage display" seems to respect an expression and interaction system of proteins fused to bacteriophages, which allow a scan in cells, tissues or organs looking for receptor-ligand pairs; said lingands are proteins which are linked to receptors present on the target under study.

As already used, the term "mutated nucleotide sequence" or "mutation" or "mutagenized nucleotide sequence" relates to the nucleotide sequence which has been mutated or changed to contain one or more nucleotides residues (for example: base pairs), and is not present in the wild-type or in the non-mutated sequence. Said mutagenesis or change consists of one or more additions, deletions, or substitutions or reallocation of acid nucleic residues.

As already used, the term "improvement of the insecticidal activity" or "improvement of the pesticidal activity" characterizes a polypeptide or an alpha-amylase inhibitor of the invention which present the improved pesticidal activity against beetles in relation to the original inhibitors which are not effective against insects. In order to measure the improvement of the pesticidal or insecticidal activity, one should require a demonstration of the presence or increase of the alpha-amylase inhibitory activity of at least 10% against the target insect, and more preferably 20%, 25%, 30%, 35%, 40%, 45%, 50%, 60%, 70%, 100%, 200% or a further increase of inhibition of the alpha-amylase activity regarding the insecticidal activity of other existing alpha-amylase inhibitors which are active against the same insect.

The terms "inhibitor" or alpha-amylase inhibitor, or digestive enzymes inhibitor are related to a polypeptide, which present enzymatic degradation activity with anti-nutritional and insecticidal effect. It is known from the prior art that the naturally occurring alpha-amylase inhibitors are synthesized by plants, and specifically by common bean plant (*P. vulgaris*).

A person skilled in the art is aware of the advances in the molecular Biology field such as a site-specific or a random mutagenesis, methodology of the polymerase chain reaction (PCR), and techniques of the protein engineering providing an extensive collection of tools and viable protocols for the use in order to change or to engineer both amino acid sequences and gene sequences disguised as proteins of agricultural interest. Therefore, the pesticidal proteins of the invention can be changed in many ways, including amino acid substitution, deletions, truncations, and insertions. Methods for said manipulations are generally known from the prior art. For example, a variant amino acid sequence of the pesticidal protein of the present invention can be prepared by the introduction of mutations inside a synthetic nucleic acid (for example: DNA molecule). Methods for mutagenesis and amendments in acid nucleic are well described in the prior art.

One can understand that the polypeptides of the invention can be produced for both the expression of a nucleic acid herein described, and by the use of standard molecular Biology techniques.

One can describe that a method for controlling a pest can be characterized by comprising the following steps: a) Detecting the occurrence of the pest in an environment; b) Promoting the contact of the pest with a pesticidal protein isolated or produced as a composition of the present invention.

It is known that pesticidal proteins can be oligomeric and range in molecular weight, number of residues, peptide components, activities against particular pests, and other characteristics. However, through the methods described herein, active proteins against a variety of pests can be isolated and characterized. The pesticidal proteins of the invention can be used in combination or other proteins insecticides, for instance Bt δ-endotoxins to increase the action in the target insect. Furthermore, the use of pesticidal proteins of the present invention in combination with Bt δ-endotoxins or other insecticidal principles of a different nature can have a particular use for the prevention and/or handling of the insect resistance. Other insecticidal principles have said particular use, but are not limited to other types of protease inhibitors (both serine and cysteine), lectins, and peroxidases.

The invention also relates to transformed plants with at least one nucleic acid of the present invention, with a chimeric gene comprising the nucleic acid, or with a binary vector comprising the chimeric gene. Preferably, the microorganism is one that multiplies in plants. More preferably, the microorganism is a root colonizing bacterium. An embodiment of the present invention relates to an encapsulated pesticidal protein, which comprises a transformed microorganism comprising at least one pesticidal protein of the invention.

The invention also provides a method of increasing the range of the target insect through the use of pesticidal proteins of the invention in combination with at least one second pesticidal protein which is different from the pesticidal protein of the invention. Any pesticidal protein known from the prior art can be used in the method of the present invention. Said pesticidal proteins include said method, but are not limited to Bt δ-endotoxins, protease, lectins, alpha-amylase, lipid acyl hydrolases, and peroxidases inhibitors.

The invention also comprises transgenic or transformed plants comprising at least one nucleotide sequence of the invention. Preferably, the plant is stably transformed with a chimeric gene, comprising at least one nucleotide sequence of the invention operationally linked to a promoter directing the expression in plant cells. As already used, the term "transgenic plants" or "transformed plants" relates to a plant which comprises inside its genome, a heterologous polynucleotide. Generally, the heterologous polynucleotide is integrated with the genome of a transgenic plant in a stable form so that the polynucleotide can be passed to successive generations. The heterologous polynucleotide can be integrated with the genome alone or as part of a recombinant vector.

As already used, the term "transgenic" includes any cell, cell line, callus, tissue, part of the plant, or genotype of the plant which has been changed by the presence of the heterologous nucleic acid including said transgenics initially changed as well as those ones created by sexual crossing or sexual propagation of the sexual transgenic.

The term "plants" relates to photosynthetic organisms, both eukaryotes and prokaryotes, wherein the term "developed plants" relates to eukaryotic plants. The term relates to whole plants, plant organs (for example: leaves, stems, roots, flowers etc), seed, plant cells, and progeny thereof. Parts of the transgenic plants are also included in the scope of the invention comprising, for instance, plant cells, protoplasts, tissues, callus, embryos, as well as flowers, ovules, stems, fruits, leaves, roots originated from transgenic plants or its progeny previously transformed with a DNA molecule of the invention and, therefore, consisting of at least part of the transgenic cells, and are also object of the present invention. The nucleic acids of the invention can be used to impart desired treatment in essentially any plant. Therefore, the invention has the use on various plant species, including species of the genres *Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna*, and *Zea*. Particularly, the present invention relates to transformed cotton plants with the nucleotide sequences of the present invention as well as fragments and derivatives thereof, more specifically transformed plants of *Gossypium hirsutum*.

Transformation protocols as well as protocols for introducing nucleotide sequences in the plants may vary depending on the type of the plant or on the plant cell, for example, monocotyledons or dicotyledons, targets of the transformation. Viable methods of introducing nucleotide sequences in plant cells and the subsequent insertion in the plant genome are well described in the prior art and may be, but not limited to the techniques such as electoporation and microinjection of protoplasts of plants cells, or a construction can be introduced directly in the plant tissue using ballistic methods, such as bombardment with DNA-coated particles.

Microinjection techniques are known from the prior art and well described in scientific and patent literature (Zhou, G., Wang, J., Zeng, Y., Huang, J., Qian, S., Liu, G., Introduction of exogenous DNA into cotton embryos. Meth. in Enzymol., 101, 433-448, 1983) (as mentioned in patent application U.S. Pat. No. 4,743,548). The introduction of gene constructs using precipitations of polyethylene glycol is described in in Paszkowski et al. (Paszkowski, J., Shillito, R. D., Saul, M., Mandak, V., Hohn, T. Hohn, B., Potrykus, I., Direct gene transfer to plants. Meth. in Enzymol., 3, 2717-2722, 1984) (as mentioned in patent application US20020152501). Electroporation techniques are described in Fromm et al (Fromm, M. E., Taylor, L. P. Walbot, V., Expression of genes electroporated into monocot and dicot plant cells. Proc. Natl. Sci. USA 82:5824, 1985) (as mentioned in patent application US20020152501). Ballistic transformation techniques are described in Klein et al (Klein, T. M., Wolf., E. D., Wu, R., Sanford, J. C., High velocity microprojectiles for delivering nucleic acids into living cells. Nature 327:70-73, 1987) (as mentioned in patent application US20020152501). Alternatively, the gene constructs can be combined with T-DNA flanking regions appropriate and introduced in a conventional vector, the host *Agrobacterium tumefaciens*. The virulence function of the host *Agrobacterium tumefaciens* will direct the insertion of the gene constructs and adjacent marker in the DNA of the plant cell when the cell is infected by the bacterium. Transformation technique mediated by *Agrobacterium tumefaciens*, including disarmament and the use of binary vectors, are well described in the scientific literature (as mentioned in patent application US 20020152501, Horsch, R. B., Fraley, R. T., Rogers, S. G., Sanders, P. R., Lloyd, A., Hoffmann, N. Inheritance of functional foreign genes in plants. Science 233:496-498, 1984; e Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., Woo, S. C. Expression of bacterial genes in plant cells. Proc. Natl. Acad. Sci. USA 80:4803, 1983). Transformed plant cells derived from any of the transformation techniques described above can be cultivated to regenerate a whole plant which has the transformed genotype and then the desired phenotype, such as resistance to insects. Such regeneration techniques rely on the manipulation of certain phytohormones in tissue culture growth medium, typically containing a biocidal and/or herbicidal marker, which must be introduced with the desired nucleotides sequence. Plant regeneration from protoplast culture is described in Evans et al (Evans, D. E., and Bravo, J. E., Protoplasts Isolation and Culture, Handbook of Plant Cell Culture, vol. 1, 124-176, MacMillan Publishing Company, New York, 1983); and Binding 1985 (Binding, H., Regeneration of Plants, Plant Protoplasts, pp. 21-73, CRC Press, Boca Raton, 1985) (as mentioned in patent application US20020152501). The regeneration can also be obtained through the callus plant, explants, organs, or part thereof. Said regeneration techniques are generally described in Klee et al (Klee, H., Horsch, R., Rogers, S., *Agrobacterium*-mediated plant transformation and its further applications to plant biology. Ann. Ver. Of Plant Phys. 38:467-486, 1987 (as mentioned in patent application US20020152501). A gene coding for a pesticidal protein of the invention can be introduced through a viable vector in a microbial host, and said host can be inserted in plants or in animals. The term "introduced" in the context of inserting a nucleic acid in a cell means "transfection" or "transformation" or "transduction" and includes the incorporation of a nucleic acid in a prokaryotic or eukaryotic cell wherein the nucleic acid can be incorporated into the genome of the cell (for example: chromosome, plasmid, plastid, or mitochondrial DNA), converted into an autonomous replicon, or transiently expressed (for example: mRNA transfected). The term "microorganism" is herein defined as microbes which have functional organelles inside their capsules or cells as bacteria, protozoa, unicellular fungi and unicellular algae.

There are several viable methods to introduce a gene expressing the pesticidal protein inside a host microorganism under conditions allowing the maintenance and stable expression of the gene. For example, expression vectors can be constructed containing the nucleotide sequence of interest operationally linked to regulatory signals of transcription and translation for the expression of the nucleotide sequence. When an internal homologous nucleotide sequence of the organism is found with the sequence in the binary vector, there may be a recombination between said sequences and the gene which encodes the pesticidal protein will be integrated with the genome of the host organism in a stable form.

Viable host cells, wherein the cells containing the insecticidal protein will be treated to extend the activity of the insecticidal protein in the cell, when the treated cell is applied in the environment of the target pest, can include prokaryotes or eukaryotes, normally being limited to those cells which do not produce toxic substances in superior organisms. However, organisms which produces toxic substances in superior organisms can be used where the toxin is unstable or wherein the application level is sufficiently low to avoid any possibility of toxicity to mammals hosts. The hosts are particularly prokaryotic and eukaryotic less developed as fungi. Examples of prokaryotics, both gram negative and gram positive, are included, but not limited to Enterobacteriaceae, such as *Escherichia, Erwinia, Shigella, Salmonella*, and *Proteus*; Bacillaceae; Rhizobiceae, such as *Rhizobium*; Spirillaceae, such as *Photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among the eukaryotes the fungi can be exemplified, such as *Phycomycetes* and *Ascomycetes*, which includes yeast, such as *Saccharomyces* and *Schizosaccharomyces*; and *Basidiomycetes*, such as *Rhodotorula, Aureobasidium, Sporobolomyces*, and the like.

Characteristics of particular interest in selecting a host cell for the purpose of producing the insecticidal protein include the facility of introducing the gene of the insecticidal protein in the expression system, expression efficiency, stability of the protein in the host, and the presence of auxiliary genetic capabilities.

Host organisms of particular interest include yeast, such as *Rhodotorula* spp., *Aureobasidium* spp., *Saccharomyces* spp., and *Sporobolomyces* spp., *Pichia pastoris, Saccharomyces cerevisiae, Bacillus thuringiensis, Escherichia coli, Bacillus subtilis*, and the like.

The embodiments of the present invention can be effective against a variety of pests. For the purposes of the present invention, the pests are included, but not limited to insects, fungi, bacteria, nematodes, mites, protozoa pathogens, animal parasites, and the like. Pests of particular interest are insect pests, particularly insect pests which cause significative damage for agricultural plants. One can understand "insect pests" insects and other similar pests such as, for instance, insects of the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, especially *Anthonomus grandis, Diabrotica virgifera* and Lepidoptera. The insect pests of the present invention of the most cultivars are included, but are not limited to: *Ostrinia nubilalis, Agrotis ipsilon, Helicoverpa zea, Spodoptera frugiperda, Diatraea grandiosella, Elasmopalpus lignosellus, Diatraea saccharalis, Diabrotica virgifera virgifera, Diabrotica longicornis barberi, Diabrotica undecimpunctata howardi, Melanotus spp., Cyclocephala borealis, Cyclocephala immaculata, Popillia japonica, Chaetocnema pulicaria, Sphenophorus maidis, Rhopalosiphum maidis, Anuraphis maidiradicis, Blissus leucopterus leucopterus, Melanoplus femurrubrum, Melanoplus sanguinipes, Hylemya platura, Agromyza parvicornis, Anaphothrips obscrurus, Solenopsis milesta, Tetranychus urticae; Sorgo: Chilo partellus, Spodoptera frugiperda, Helicoverpa zea, Elasmopalpus lignosellus, Feltia subterranea, Phyllophaga crinita, Eleodes, Conoderus*, and *Aeolus* spp., *Oulema melanopus, Chaetocnema pulicaria, Sphenophorus maidis, Rhopalosiphum maidis, Sipha flava, Blissus leucopterus leucopterus, Contarinia sorghicola, Tetranychus cinnabarinus, Tetranychus urticae; Pseudaletia unipunctata, Spodoptera frugiperda, Elasmopalpus lignosellus, Agrotis orthogonia, Elasmopalpus lignosellus, Oulema melanopus, Hypera punctata, Dia-*

*brotica undecimpunctata howardi, Schizaphis graminum, Macrosiphum avenae, Melanoplus femurrubrum, Melanoplus differentialis, Melanoplus sanguinipes, Mayetiola destructor, Sitodiplosis mosellana, Meromyza americana, Hylemya coarctata, Frankliniella fusca, Cephus cinctus, Aceria tulipae; Cylindrocupturus adspersus, Smicronyx fulus, Smicronyx sordidus, Suleima helianthana, Homoeosoma electellum, Zygogramma exclamationis, Bothyrus gibbosus, Neolasioptera murtfeldtiana; Heliothis virescens; Helicoverpa zea; Spodoptera exigua; Pectinophora gossypiella; Anthonomus grandis; Aphis gossypii; Pseudatomoscelis seriatus; Trialeurodes abutilonea; Melanoplus femurrubrum; Melanoplus differentialis; Thrips tabaci; Franklinkiella fusca; Tetranychus cinnabarinus; Tetranychus urticae; Diatraea saccharalis, Spodoptera frugiperda, Helicoverpa zea, Colaspis brunnea, Lissorhoptrus oryzophilus, Sitophilus oryzae, Nephotettix nigropictus, Blissus leucopterus leucopterus, Acrosternum hilare; Pseudoplusia includens, Anticarsia gemmatalis, Plathypena scabra, Ostrinia nubilalis, Agrotis ipsilon, Spodoptera exigua, Heliothis virescens, Helicoverpa zea, Epilachna varivestis, Myzus persicae, Empoasca fabae, Acrosternum hilare, Melanoplus femurrubrum, Melanoplus differentialis, Hylemya platura, Sericothrips variabilis, Thrips tabaci, Tetranychus turkestani, Tetranychus urticae; Ostrinia nubilalis, Agrotis ipsilon, Schizaphis graminum, Blissus leucopterus leucopterus; Acrosternum hilare, Euschistus servus, Jylemya platura, Mayetiola destructor, Petrobia latens; Vrevicoryne brassicae, Phyllotreta cruciferae, Phyllotreta striolata, Phyllotreta nemorum, Meligethes aeneus, Meligethes rufimanus, Meligethes nigrescens, Meligethes canadianus*, and *Meligethes viridescens; Leptinotarsa decemlineata* and *Zabrotes subfasciatus; Calossobruchus* spp., *Acanthoscelides obtectus*. The examples below are placed so that to illustrate and better elucidate the invention and cannot be taken as a form of limiting the present invention.

EXAMPLES

Usual techniques of molecular biology (for example: bacteria transformation and electrophoresis in nucleic acid agarose gel) are described through the terms commonly employed. Details of the practice of such techniques are described in Sambrook et al (Sambrook, J., Russell, D. W., Molecular Cloning, A Laboratory Manual, 2nd ed., Cold Spring Harbor Laboratory Press. 1989). Example 1—Alpha-amylases enzymatic extraction, purification and characterization of the boll weevils.

The alfa-amilases of the boll weevils were obtained for the use in the selection of related genes, starting from a variant genes combinatorial library of alpha-amylase inhibitors.

Figure 2:
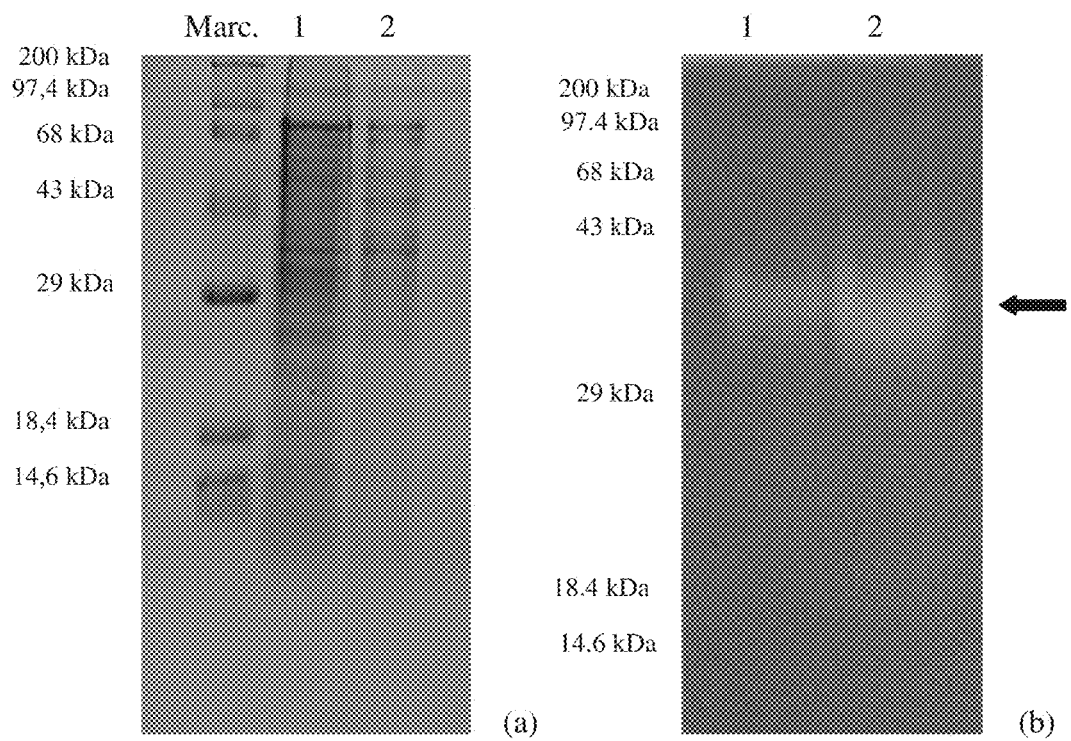
FIG. 2. (a) Analysis of the electrophoretic profile in polyacrylamide gel of the proteins fractions eluted in the chromatography (b) Zymogram indicating the presence of α-amilase due to the degradation of the iodine used for coloring the gel (light region indicated with an arrow) (Marc.) Molecular mass indicator; (1) crude protein extract; (2) Percentage value of the group of peak fractions showing enzymatic activity (FIG. 1).

Third instar larvae grown on artificial diet were macerated in 500 µL of extraction solution (10 µM of E-64 and 5 µg/mL pepstatin A) and centrifuged at 10.000 g, 4° C., and 30 min. The supernatant was collected and filtered, using filter of 0.45 µm. The protein extract was quantified as described by Bradford (Bradford, M. M. A rapid and sensitive method for the quantitation of microgram quantities of protein using the principle of protein-dye binding. Analitical Biochemical, 72:248-254. 1976.) The total extract was submitted to hydrophobic chromatography using the CL 4B Phenyl sepharose resin, made by Amershan®. The resin was pre-balanced with E Buffer (10 mM of pH 6.0 imidazole, 1M of $(NH_4)_2SO_4$). The protein sample was applied, and the non-binding proteins were subsequently washed with E buffer. The proteins absorbed to the resin were eluted using a linear gradient of 1M of ammonium sulfate $(NH_4)_2SO_4$ at 0 M, in fractions of 1 mL (flow 1 mL. min-1) and the absorbance was measured in 280 nm. The collected fractions were analized in in vitro assay as to the presence of amylolytic activity. An aliquot (2 µL) of each fraction was incubated for 30 min to 25° C. with 68 µL of Buffer activity (50 mM of pH 5.8 sodium phosphate, 200 mM of NaCl, 0.1 mM of CaCl2) and 30 µL of starch solution 0.125% (p/v), solubilized in the same Buffer. The amylolytic activity was detected after the addition of 140 µL of iodine solution (0.01% marketed iodine dye, 125 mM of HCl) and measured by the absorbance in 630 nm. The fractions presenting amylolytic activity (eluted in the range between 0.2167 to 0 M of $(NH_4)_2SO_4$) (FIG. 1) were grouped, dialyzed against water and concentrated in vacuo. After purity analysis using gel electrophoresis in SDS-PAGE12% (Lammeli U. K., Cleavage of Structural Proteins during the Assembly of the Head of Bacteriophage T4. Nature 227: 680-685, 1970) (FIG. 2) the semi-purified amylolytic activity of proteins in the hydrophobic chromatography was confirmed by the application in zymogram. After the separation of the proteins in the electrophoresis, the gel was incubated for 1 h in solution 2.5% of TritonX-100 (v/v) at room temperature, for the renaturation of the alpha-amylases. It was followed by the incubation in activity buffer (described above), for 4 h, 37° C. and staining with iodine solution. The bands indicating amylolytic activity stood out because of its white color in the gel stained of blue (FIG. 2b).

Example 2

Generation of mutant genes effective in controlling the *A. grandis*, produced as from the mixture and the recombination of the native genes αAI-1 and αAI-2, by the application of the DNA shuffling technique.

The construction of the Recombinant gene library analogous to the genes αAII-1 e αAI-2, derived from beans, is an important biotechnological approach, importantly contributing in plant improvement programs, through genetic transformation to generate transgenics. Such technology provides a range of new molecules with use potential in the transformation of plants aiming at the control of the target insect, as well as the improvement of the insecticidal activity of new proteins coded by the recombinant genes. Such factor becomes even more relevant when low levels of expression of said heterologous proteins in genetically transformed plants are considered.

Once having the presence starch grains identified in the reproductive structure of the cotton plant bud, preferred location for feeding by the insect pest *A. grandis*, and also having the presence of two forms of the alpha-amylase enzyme evidenced, super expressed, in the insect larvae, the strategy of obtaining in vitro new genes, analogous to the genes αAI-1 e αAI-2, coders for alpha-amylase inhibitors began. Thus, native gens αai-1 and αAai-2 were individually amplified by PCR with specific oligonucleotides for the gene sequence involved, which contain the sequence of the restriction enzyme SfiI (5'GGCCNN NNNGGCC3') (SEQ ID NO: 9). Said oligonucleotides were designed in our laboratory using as templates the native gene sequences αAI-1 (Genbank: EF087992.1) and αAI-2 (Genbank: D26109 and AJ439565) and they introduce to the end 5' and 3' of the native genes, the sequence of said enzyme (sense oligonucleotides SfiIAI1F-5' CCCGGCCCAGGCGGC CGCCACCGAAACCTC 3' (SEQ ID NO: 10) and SfiIAI2F CCCGGCCCAGGCGGCCGCCAGCGACACCTC 3' (SEQ ID NO: 11) and antisense oligonucleotides SfiIAIR 5'CCGGCCGGCC TGGCCGAGGATCTTGTTGAG 3' (SEQ ID NO: 12) and SfiIA2R 5' CCGGCCGGCCTGGCCGAGGATATTGTTGAG 3' (SEQ ID NO: 13) are used in a reaction of PCR with final volume of 50 µL, containing 375 nM of each specific oligonucleotide, 200 nM of dNTPs, 1 X of the buffer for the taq (Pfu)(Promega) enzyme, 3 U of DNA taq (Pfu)(Promega) polymerase and 400 ng of each DNA αai-1 and αai-2 in its original vectors. The amplification was conducted in thermocycler (Mastercycler Gradient—Eppendorf) under the following conditions: prior denaturation at 95° C. for 5 minute, a repetition of 29 cycles at 95° C. for 45 seconds (denaturation); 55° C. for 45 seconds (annealing of the oligonucleotides) and at 72° C. for 90 seconds (extension of the DNA polymerase) and at the end an extension at 72° C. for 10 minutes.

The reaction generates a product of 660 pb (base pairs), which was submitted to a electrophoresis in 1% agarose gel, at 100 Volts for 90 minutes. The gene fragment was excised and eluted from the agarose gel using the kit Geneclean® II (Qbiogene).

Figure 3:
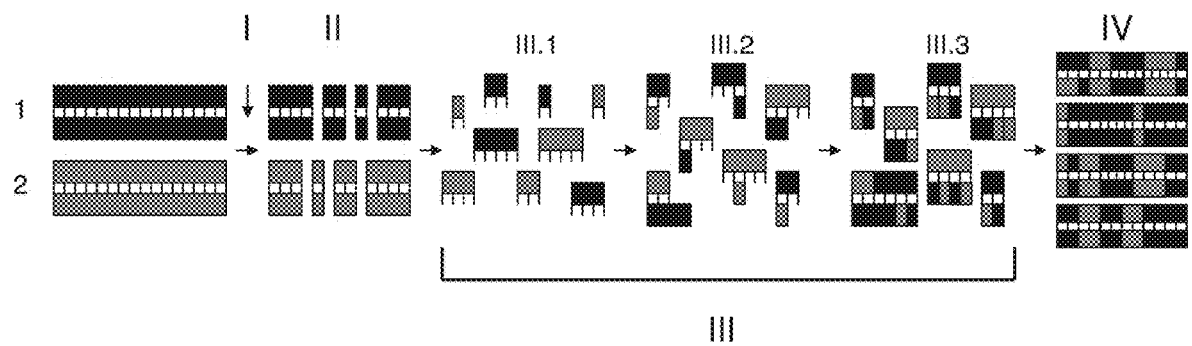
FIG. 3. DNA Shuffling utilizing two genes as substrate and analysis of the amplification of the population of analogous mutant αAIs genes with specific oligonucleotides for insertion of the restriction site into the SfiI enzyme. Product fragmented with DNase (II), amplifications (III) and reconstruction of the analogous mutant genes (IV) analyzed on 2.5% agarose gel.

Following the protocol of the technique of DNA shuffling described by Stemmer, W. P. C. et al., (Stemmer, W. P. C. Rapid evolution of a protein in vitro By DNA shuffling. Nature. London, 370:389-391, 1994) and Zhao & Arnold (Zhao, H. and Arnold, F. H. Functional and nonfunctional mutations distinguished by random recombination of homologous genes. Proc. Natl. Acad. Sci. USA., 94:7997-8000, 1997), digestion was performed with the nuclease DNAase I of the mixture containing 5 µg of each new DNA product (SfiI/αai-1/SfiI and SfiI/αai-2/SfiI) amplified by PCR and purified from agarose gel. The reaction of the lyophilized mixture was conducted in 80 µL of enzyme buffer (50 mM tris pH 7.5, 1 mM MnCl2, 0.1 mg/mL of BSA) with 0.03 U of DNAse I enzyme (FIG. 3: steps I and II) and interrupted by the addition of 250 mM of EDTA (4-acetic acid 2-amino ethylene). After such step, the gene product is completely fragmented generating gene pieces of 50 to 300 pb (FIG. 4.2), which were purified from the 2.5% agarose gel using the column of the Kit PCR Purification® (QIagen). The purified fragments were used in a PCR reaction, which followed the following conditions: 10 µL of the pure product digested with DNAse I, 1× of the Taq Pfu buffer, 0.4 mM of dNTPs, 0.1 U of Taq Pfu (Promega), totalizing 25 µL. The PCR reaction was conducted in thermocycler (Mastercycler Gradient—Eppendorf) under the following conditions: Prior denaturation at 95° C. for 2 minutes, a repetition of 43 cycles at 95° C. for 1 minute (denaturation); 55° C. for 1 minute (annealing of fragments) and 72° C. for 1 minute with an increase of 5 second per cyclo (extension of the DNA polymerase) and at the end an extension at 72° C. for 7 minutes.

Figure 4:
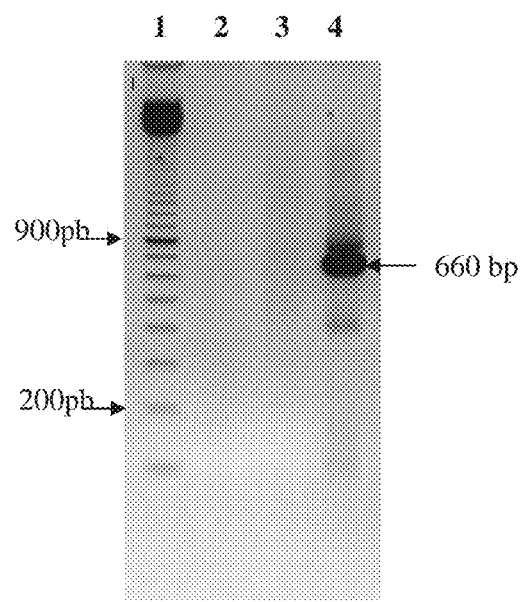
FIG. 4. Analysis on 2.5% agarose gel of the product for reconstruction of the analogous mutant genes. (1) molecular mass marker, (2) percentage value of the product of degradation with DNAse I; (3) Product of amplification without using oligonucleotides (step III, Figure), utilizing the product of fragmentation as a model; (4) Product of the amplification utilizing specific oligonucleotides—reconstruction of the population of analogous mutant genes (660 bp). The arrow indicates the size of the original genes.
Figure 5:
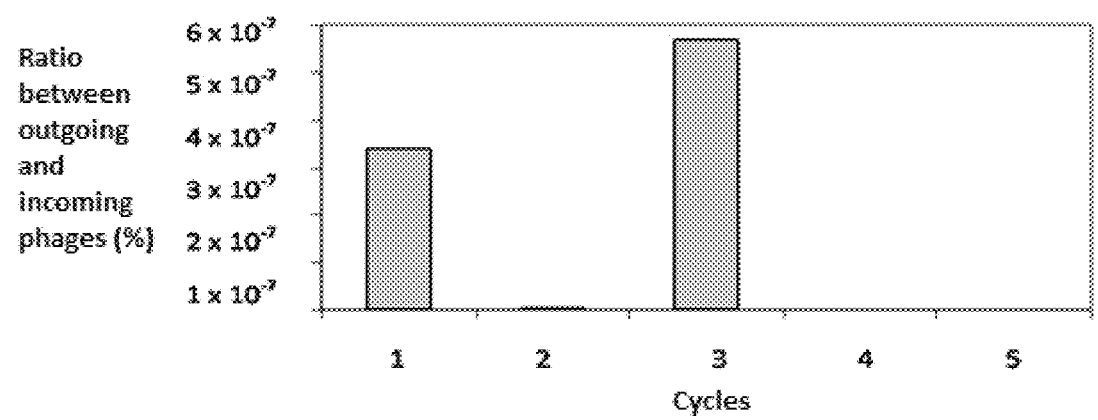
FIG. 5. Chart containing the result of the monitoring of enrichment of specific phages, obtained during selection. Identification of the selection cycle indicating the group with the highest number of specific phages.

Said DNA shuffling reaction is conducted without the addition of oligonucleotides, generating at the end an amount of various size fragments (FIG. 4.3). Said new product is then used in the second PCR reaction as template, in the following conditions: 6% of the product volume of the first reaction (template), 1× of the buffer Taq Platinum, 0.2 mM dNTPs, 0.8 µM of the specific oligonucleotides SfiI F and SfiI R, and 2.5 U in the mixture of 1:1 (v/v) Taq Pfu (Promega)/Taq DNA polymerase (Invitrogen). The amplification reaction was conducted in thermocycler (Mastercycler Gradient—Eppendorf) under the following conditions: Prior denaturation at 95° C. for 2 minutes, a repetition of 10 cycles at 95° C. for 30 seconds (denaturation); 55° C. for 30 seconds (annealing of the fragments), 72° C. for 45 seconds (extension of the DNA polymerase), another repetition of 14 cycles at 95° C. for 30 seconds (denaturation), 55° C. for 30 seconds (annealing of the product), 72° C. for 45 seconds (extension of the DNA polymerase) with an increase of 20 seconds per cyclo and at the end an extension at 72° C. for 7 minutes.

Thus the original gene is reconstituted with modifications in its nucleotide structure, by the introduction, deletion or by the nucleotide substitutions. Such final reconstructed product was submitted to a 1% agarose gel electrophoresis, at 100 Volts for 90 minutes, excised and eluted from the gel with the Kit Geneclean® II (Qbiogene) (FIG. 4.4). The purified product, approximately 1 µg, was then digested with the restriction enzyme SfiI for 16 h at 50° C. and submitted to 1% agarose gel electrophoresis, at 100 Volts for 90 minutes. The band in the approximate size of the original gene without the signal sequence (approximately 660 pb) was excised from the gel and the DNA was eluted by the Geneclean® II Kit (Qbiogene) (FIG. 4.4).

The final product (population of recombined genes) with specific adapters becomes suitable for cloning in the pCOMB3X vector (Andris-Widhopf, J.; Rader, C.; Steinberger, P.; Fuller, R., Barbas III, C. F. Methods for the generation of chicken monoclonal antibody fragments by Phage display. Journal of Immunological Methods, 242: 159-181, 2000). Thus, the new reconstructed genes (analogous to the parental genes αAI-1 and αAI-2) were cloned in the vector with assistance of the T4 ADN Ligase® enzyme (Invitrogen) and such vector to transform cells of *Escherichia coli* XL1-Blue® (Stratagene), through electroporation, under the following conditions: 25 uFD capacitance, resistance 200 □, voltage 2.5 KVolts. The transformants were then seeded into plates containing Luria-Bertani Agar and carbenicillin USB (100 µg/mL) culture medium. After 17 hours at 37° C. the colonies grown separately on selective medium indicate the title of the library containing 107 transformants.

Figure 8:
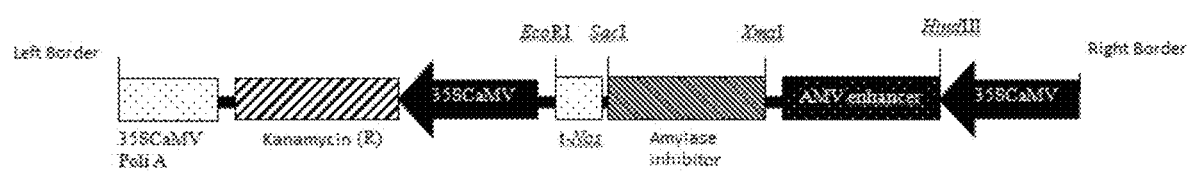
FIG. 8. Map of the vector constructed for expression in *Arabidopsis* plants. Schematic representation of the vector, including the duplicated 35S promoter, enhancer of alfalfa mosaic virus and the nopaline synthetase terminator.

Such αAIs analogous library generated by DNA shuffling and fused to the protein III of the filamentous phage M13 capsid (fusion phage) was then selected by the presentation technique of the proteins in the bacteriophage surface—Phage Display (Barbas III, C. F.; Burton, D. R., Scott, J. K., Silverman, G. J. Selection from antibody libraries. In: Phage display—A Laboratory Manual—USA: Cold Spring Laboratory, 10.1-10.20, 2001) using as alpha-amylases bonders of *A. grandis* (Francis, B. R., Maaty, W. S. A., Bulla-Jr, L. A. Effects of Midgut-Protein-Preparative and Ligand Binding Procedures on the Toxin Binding Characteristics of BT-R1, a Common High-Affinity Receptor in *Manduca sexta* for CrylA *Bacillus thuringiensis* Toxins. Applied and Environmental Microbiology. June 1998, Vol. 64, No. 6, p. 2158-2165). The cultivation of transformed *E. coli* XL1-Blue cells, in SB medium containing 100 μg mL-1 carbenicillin, 5 μg mL-1 tetracycline was incubated at 37° C. with stirring until reaching an optical density of A550=0.6-0.8. Then, 1×1012 pfu mL-1 of the adjuvant phage (VCSM13□ Stratagene) was added to produce fusion phage containing the analogous of αais, incubated for 2 h at 37° C. Kanamycin 100 μg mL-1 was added and the incubation continued for 12 h at 37° C. The cells collected by centrifugation were stored at −20° C. for further DNA preparation. The fusion phage were precipitated with PEG-8000 (4% w/v) during 30 minutes in the ice and after centrifugation, they were resuspended in 2 mL of 1% (w/v) ASB (Bovine Serum Albumin) in saline solution. Collected after centrifugation, the preparation of fusion phage is used in the selection cycles.

In the binding affinity selection procedure, os fused phage were deposited in microtiter plate wells previously sensitized with *A. grandis* (100 rig) alpha-amylase, extracted from the membrane of the boll weevils bowel. At each selection cyclo, the wells are washed with PBS-Tween solution (137 mM NaCl, 2.7 mM KCl, 12 mM Na2HPO4, 1.2 mM KH2PO4 and 0.05% Tween 20□) and, the specific phages eluted in low pH, are used to transfect new *E. coli* cells. The amplified phage particles are used in the successive selection cyclo. The procedure envolved five wash, elution and amplification cycles. The titration of the colonies collected in each cycle is performed by the colony plating in serial dilutions in SB-agar medium containing 100 μg mL-1 carbenicillin. The isolated colonies of the specific amount of phage eluted in the third selection cyclo (presenting the biggest title, therefore, the specific phage Enrichment cyclo) (FIG. 5) were amplified with specific oligonucleotides for the □ais genes. Colonies showing amplification in PCR and containing approximately 600 pb (parental gene size) were selected for the expression in Top 10 F' line *E. coli.*

The original genes and the analogous genes selected in the third selection cyclo were used to transform the *E. coli*. The transformation product was plated in LB-agar medium with 100 μg mL-1 amplicilin and grown at 37° C. for 16 h. The gene integrity was determined by PCR and 86 clones containing the entire gene were pre-inoculated in 2×YT selective medium (1% Yeast Extract, 1.6% peptone, 1.0% NaCl, pH 7.0 containing 0.5% glucose and 100 μg mL-1 amplicilin) in a plaque containing 96 wells of 2 mL, with incubation of 16 h at 37° C. and 220 rpm (revolutions per minute). Subsequently, 10 μL of the inoculants were incubated in 1 mL of SB medium (1% MOPS, 3% tryptone, 2% yeast extract, 7.0 pH with 100 μg mL-1 amplicilin) at 37° C., 220 rpm (revolutions per minute) until Abs600 nm between 0.6-0.8. The expression was induced by the addition of 1 mM of IPTG (thio-β-galactoside) with incubation of 12 h, 30° C., 200 rpm. The culture was centrifuged and the supernatant collected was maintained at 4° C., used in the dot blot.

For the expression analysis of the 86 clones (dot blot), the aliquot of the preparation (supernatant) was directly deposited on the nitrocellulose membrane (Hybond C® Amersham) and said membrane was hybridized against anti-HA primary antibody (hemagglutinin) (Biotechnology Santa Cruz), followed by incubation with anti-IgG produced in rabbits (Sigma) and conjugated to alkaline phosphatase. The expression signal were detected after NBT (Nitro Blue Tetrazole)/BCIP (5'bromo 4-chloro-indolyl-Phosphate®—Roche) revelation. Thus, 31 clones were identified and expressed by the procedure and the sequence of 26 clones was determined by the sequencing reaction in the following conditions: Plasmid DNA 400-800 ng containing the analogous and specific oligonucleotides 4 pM (SfiIAIfsR and SfiIAIfsF) in an automatic sequencer model 3130 xL Genetic Analyzer (APPLIED BIOSYSTEMS).

The multiple alignment of 26 sequences of the analogous clones was performed with the sequences of the αAIs original genes by the CLUSTALW (http://www.ebi.ac.uk/Tools/clustalw2/) (Larkin, M A; Blackshields, G; Brown, N P; Chenna, R; McGettigan, P A; McWilliam, H; Valentin, F; Wallace, I M; Wilm, A; Lopez, R; Thompson, J D; Gibson, T J; Higgins, D G. ClustalW and ClustalX version 2. Bioinformatics. 2007; 23:2947-2948. doi: 10.1093/bioinformatics/btm404)—The recombination profile (mutations distribution) (FIG. 6 and FIG. 7) determined for the selected analogous can be classified in 3 distinct groups: In 17 of the mutant analogous, the amino acids residue mutations were in the majority identical to the sequence of αAI-1 and in 3 others, mostly identical to the sequence αAI-2, both in more than 65% of the positions. Six of the selected mutants showed between 40-60% of sequence identity in the positions related to αAI-1 and αAI-2. Two repeated sequences were identified for two of the selected clones and one in another case, the same sequence in 3 of the selected mutant analogous.

Example 3

Construction expression vectors in model plants containing variants of alpha-amylase inhibitors and obtaining recombinant proteins in the active form.

The alpha-amylase inhibitors of bean isolate (αAI-1 and αAI-2) become active after receiving the post-translational modifications, being the heterotetrameric form the one containing two subunits α and β (9 and 14 kDa, respectively) interacting with each other. Such modification involves a proteolysis in the Asn77 residue by a specific Asn-protease and removal of residue Asn79 by a carboxypeptidase. In addition the removal of 19 residues located in c-terminal of the subunit β occurs (Young, N. M.; Thibault, P., Watson, D. C.; Chrispeels, M. J.). Post translational processing of two alpha-amylase inhibitors and an arcelin from the common bean, *P. vulgaris*. FEBS Letters, 5: 203-20, 1999)). It is known that tobacco plants and some leguminous perform such processing efficiently originating active molecules (Silva, M. C. M.; Mello, L. V.; Coutinho, M. V.; Rigden, D. J.; Neshich, G.; Chrispeels, M. J.; Grossi-de-Sá, M.F. Mutants of common bean alpha-amylase inhibitor-2 as an approach to investigate binding specificity to alpha-amylases. Brazilian Agricultural Research, 39:201-208, 2004.) For the expression of the heterologous proteins, the expression binary vector was used in pCambia2300 plants provided by Canbia, Camberra (Australia). Initially, the vector was modified to receive the expression cassette containing: The promoter 35S of the duplicated cauliflower mosaic virus (CamV35Sd), the AMV "enhancer" of the alfalfa mosaic virus and the NOS terminator (synthase nopaline), inserted between the restriction sites EcoR I and Hind III (FIG. 8). In order to amplify the inserts through PCR (alpha-amylase inhibitors variants) cloned in pComb3X phagemid, oligonucleotides were designed and the one of sense orientation being: XmaPSAI-1 containing restriction site Xma I, αAI-1 signal peptide and end 5'(5'CCCCCCGGGATGGCTTCCTCCAACTTACTCTCCCTAGCCCTCTTCCTTGTGCTTC TCAACCACGCAAACTCAGCCACCGAAACCTCC 3') (SEQ ID NO: 14) and the antisense, AI-2SacI, compound by the restriction site Sac I and stop codon (5' CCCGAGCTCTTAGAGGATCTTGTTGAGGAC 3') (SEQ ID NO: 15). Said oligonucleotides were then used in a PCR reaction with final volume of 50 μL, containing 300 nM of each oligonucleotide, dNTPs 240 μM, 1 X of the buffer for the Taq polymerase (Invitrogen) enzyme, U DNA polymerase Taq (Invitrogen) 2.5 and 200 ng of the variant genes of αais cloned in pComb3X vector The amplification was conducted in thermocycler (Mastercycler Gradient—Eppendorf) under the following conditions: prior denaturation at 94° C. for 2 minute, a repetition of 25 cycles at 94° C. for 45 seconds (denaturation); 50° C. for 45 seconds (annealing of the oligonucleotides) and at 72° C. for 45 seconds (DNA polymerase extension) and at the end an extension at 72° C. for 5 minutes.

The product generated purified from agarose gel, after the electrophoresis, is digested with the Xma I and Sac I enzymes and was then submitted to a binding reaction in the following conditions: 30 ng of the insert, 100 ng of the vector (modified pCambia 2300—FIG. 8) and 1 U of T4 ADN ligase in the buffer of the enzyme (Invitrogen). The mixture was incubated at temperature of 16° C., for 16 h. *E. coli* XL-1 Blue chemically competent cells were transformed with 3 µL of the binding system by electroporation. For said procedure, the 30 ng of DNA were mixed with 40 µL of competent cells and the incubated mixture was transformed through electroporation with the 25 UFD capacitance conditions, 200☐ resistance, 2.5 KVolts voltage. The cells were immediately collected with 1 mL Luria-Bertani medium and incubated at 37° C. for 1 h. Afterwards, the cells were inoculated in 10 mL of agar Luria-Bertani culture containing 100 µg mL-1 of kanamycin and grown during 16 h, at 37° C. For the verification of positive clones, a colony PCR was conducted, which used the DNA of the transformed bacteria as template and the same described conditions for the cloning of the genes. The positive clones were then, inoculated in 5 mL of agar Luria-Bertani medium containing 100 µg mL-1 amplicilin. The DNAs were prepared and the sequences determined for the cloning confirmation containing a correct open reading phase.

For the expression of the new genes in *Arabidopsis* plants, the plasmids generated (pFSp12300AIC3—number ATCC PTA11586 containing the nucleotide sequence of SEQ ID NO: 1; pFSp12300AIG4—number ATCC PTA11584 containing the nucleotide sequence of SEQ ID NO: 3; and pFSp12300AIA11—number ATCC PTA11585 containing the nucleotide sequence of SEQ ID NO: 2) were used to transform *Agrobacterium tumefaciens* cells, line GV3101 (pMP90) (Konz, C.; Schell, J. The promoter de TL-DNA gene 5 controls the tissue-specific expression of chimaeric genes carried by a novel type of *Agrobacterium* binary vector. Molecular and general genetics 204: 382-396.1986) by thermal shock. It was added 1 µg of DNA of the pCambia2300/AIsmut vectors (FIG. 8) in 100 µL of competent cells and the incubated mixture in ice for 30 minutes, followed by solificação using liquid nitrogen. The thermal shock was performed for 5 minutes at 37° C. and the cells homogenized with LB medium 1 mL (Luria-Bertoli) preheated at 37° C. After the incubation of 2 h at 37° C., 50 µL were plated in LB-agar containing 100 µg mL-1 rifampicin; 50 µg mL-1 gentamicin and 100 µg mL-1 kanamycin and the colonies grown at 28° C., for 24-48 h. The positive transformants were confirmed by the DNA amplification in PCRs using the XmaPSAI-1 primer oligonucleotides and AI-2SacI (described above) in the conditions of 95° C. for 5 min, followed by 30 cycles of 95° C. for 45 seg, 55° C. for 45 seg and 72° C. for 90 seg, with extension of 72° C. for 10 min. The transformant colony was grown in 2 mL of LB-kanamycin (50 µg mL-1) at 28° C. with 200 rpm of stirring during 48 h. Such pre-inoculum was added to 200 mL of LB-kanamycin (50 µg mL-1) and the stirred cultivation in 200 rpm at 28° C., until getting OD 600 nm between 0.8-1.5. After the 1500 g centrifugation for 20 min., The precipitate was resuspended in 200 mL of infiltration medium (0.22% of MS salts (Murashige & Skoog-Murashige, T.; Skoog, F. A revised medium for rapid growth and bioassay with tobacco tissue cultures. Physiol Plant. 15:473-497, 1962.)) MES 0.5M (2-(N-morpholino ethanesulfonic) acid, sucrose 5 (p/v) and 0.2% of Silwet L-77, pH 5.7). Said solution was used to infiltrate the still closed buds of 3 to 5 *Arabidopsis* plants, following the procedure described by Clough & Bent (S. J. Clough, S. J.; A. Bent, A. F. Floral dip: a simplified method for *Agrobacterium*-mediated transformation of *Arabidopsis thaliana*. Plant Journal., 16:735-743, 1998). Mature seeds collected from the transformed plants were disinfected (5 min in Ethanol 70% added of Triton X-100 0.1%) and seeded in 25% MS medium, 0.8% of agar containing kanamycin 100 µg mL-1. Seedling resistant to the selective medium were transferred and developed in the soil and the leaves collected and used for the molecular characterization of the transformants. With the purpose of extracting the DNA, a leaf of the plant was macerated in 300 µL of EB buffer (Tris 200 mM, EDTA 25 mM, NaCl 250 mM, SDS 0.5%) and chloroform 100 µL, followed by strong stirring for 1 min. After the centrifugation at 11.000 g for 5 min, the superior phase was collected and the precipitated DNA with equal isopropanol volume. The precipitated was washed with 70% ethanol and the dry precipitated resuspended in 100 µL of water. For the identification of the presence of the variant genes in *Arabidopsis* plants, 3 µL of the extracted DNAs were used as template in PCRs, containing the XmaPSAI-1 and AI-2SacI oligonucleotides, for the final volume of 15 µL, in the following condition: 95° C. for 5 min, followed by 30 cycles of 95° C. for 45 seg, 55° C. for 45 seg and 72° C. for 90 seg, with extension of 72° C. for 10 min.

Figure 9:
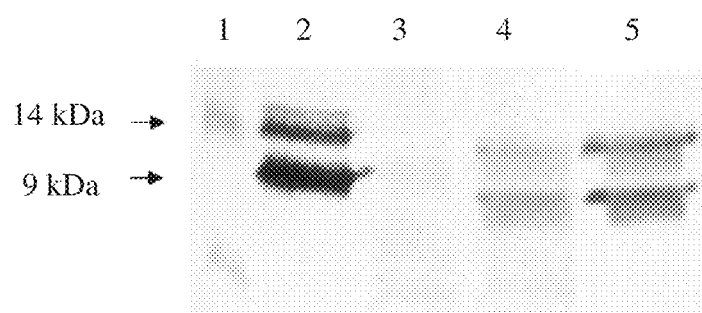
FIG. 9. Immunodetection of proteins extracted from transgenic plants containing the parental gene. Presence of mutant proteins isolated from plants transformed with the original and analogous genes, hybridized with anti-inhibiting alpha-amylase α-AI-1(2) antibody, analogous genes αAIC3 (4) and αAI-A11(5) and non-transformed plant (3). The arrows indicate the molecular mass of sub-units α (9 kDa) and β (14 kDa) of the mature protein.

The plants showing gene amplification in the PCR analysis were analyzed as to the protein expression, using the Western Blot and ELISA techniques. Protein extracts were obtained from three to four plant leaves of T2 generation macerated in liquid nitrogen. The powder was resuspended in extraction buffer (125 mM Tris-HCl pH 8.8; 0.1% SDS, 10% glycerol and 50 mM sodium metabisulfite) and after the centrifugation (9000 g for 10 min) the supernatant (protein extract) was collected and the concentration determined by the Bradforf method (Bradford, M. M. A rapid and sensitive method for the quantitation of microgram quantities of protein using the principle of protein-dye binding. Analitical Biochemical, 72:248-254. 1976). Thirty five micrograms of the protein extract were separated in SDS-PAGE 15% electrophoresis (Lammeli U. K., Cleavage of Structural Proteins during the Assembly of the Head of Bacteriophage T4. Nature 227: 680-685, 1970) and the proteins transferred to the Nitrocellulose membrane (Hybond C® Amersham). After the blocking in 3% gelatin solution in TBS for 16 h at room temperature, the membrane was incubated with anti-αAI-1 antibody produced in rabbit in the dilution of 1:700 using TBS containing 1 gelatin %, during 4 h, room temperature, under light stirring. This was followed by three washes of 15 min under stirring using TBS-T solution (TBS added of 0.05% of Tween-20) and further incubation for 2 h with secondary antibody: anti IgG conjugated to peroxidase enzyme (BioRad) produced in rabbit and 1000 times diluted in TBS. Again, 3 washes of 5 min each were given later, using TBS-T and then, the proteins were detected after the incubation of the membrane in a revelation solution comprising the mixture of the A solution (9 mg de HRP (Horseradish peroxidase) dissolved in 3 mL chilled methanol and of B solution (hydrogen peroxide (H2O2) 12 mL added in TBS 15 mL). FIG. 9 shows the detection of the recombinant analogous proteins represented in two subunits: α and β (9 kDa and 14 kDa, respectively), indicating the correct processing of the alpha-amylases inhibitory proteins.

Figure 10:
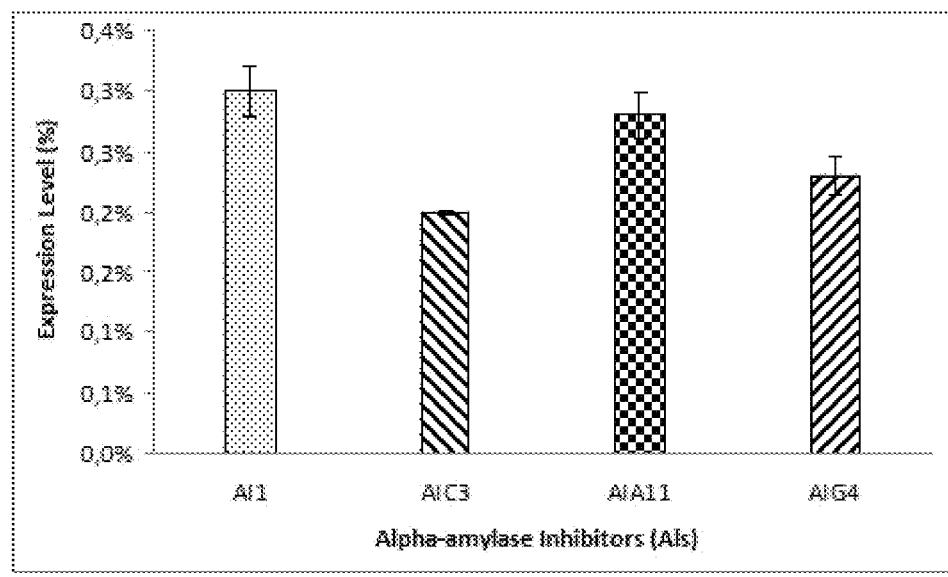
FIG. 10. Analysis on the expression of analogous αAIs genes in transgenic plants using immunoenzymatic assay (ELISA). Quantification of the expression product of the analogous αais gene in transgenic *Arabidopsis* plants.

The recombinant proteins were quantified by ELISA, sensitizing the wells of a microtiter plate with protein extract 150 µg for 2 h at 37° C. After sensitization of the wells and disposal of protein extract, the nonspecific sites were blocked with 200 µL solution (3% BSA (Bovine Serum Albumin) dissolved in TBS-T solution (TBS solution containing 0.05% of Tween-20) during 16 h at 4° C., with addition of 1 h at 37° C. The wells were washed 3 times with TBS-T and incubated with the antibody anti-αAI-1 produced in rabbit (diluted 1:750 in TBS containing 1% of BSA and 0.005% of Tween-20) during 4 h at 37° C. The washes were repeated as described above and were incubated with the secondary antibody: anti-IgG produced in rabbit and conjugated to Alkaline Phosphatase (Sigma cta. N. 3687) (diluted 1:5000 in TBS) during 2 h at 37° C. The washes followed again, as described above, and 100 µL od revelation solution was added (1 mg/mL pNPP—p-nitrophenylphosphate) dissolved in 1M diethanolamine solution containing 0.5 mM of MgCl2, pH 9.8). After the dark incubation during 45 min, the absorbance was measured in 405 nm. Based on the standard curve obtained by ELISA, using different concentrations of the α-AI-1 protein, one could observe that the concentration of the analogous inhibitors of the ones present in common beans varied from 0.01 to 0.03% in relation to the total protein (FIG. 10).

Figure 11:
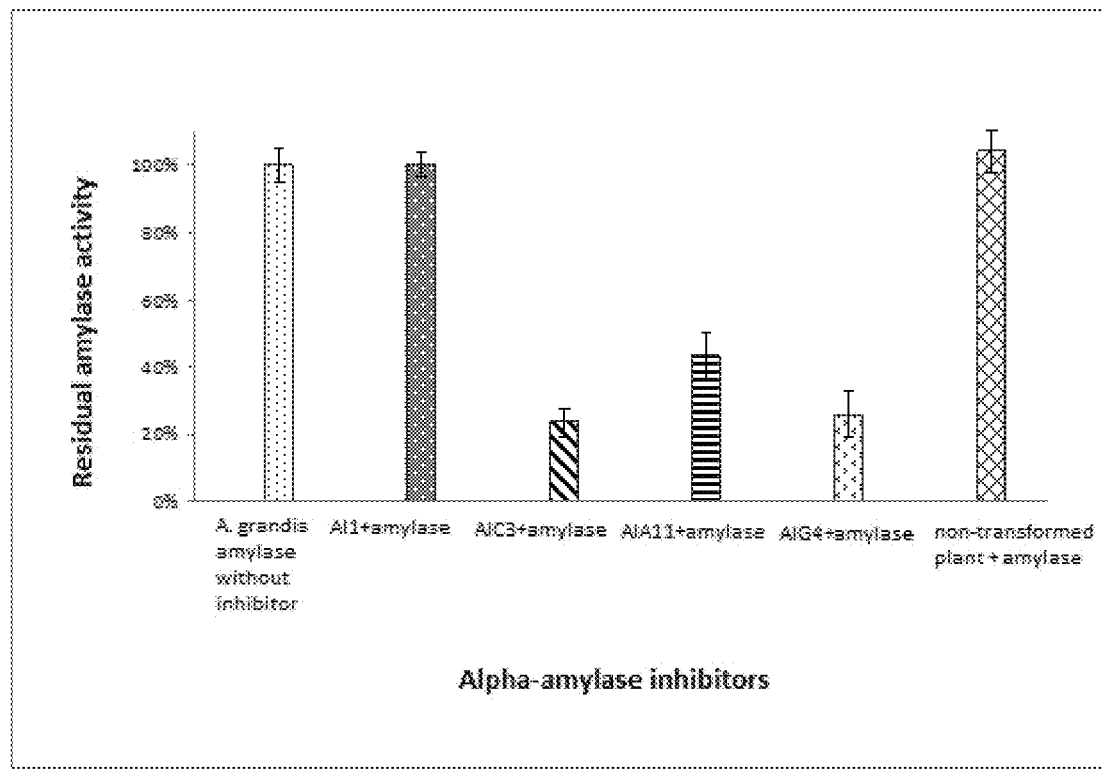
FIG. 11. Chart displaying in vitro inhibitory activity using total proteins of the selected analogous variants, expressed in model plants.

In order to determine the activity of the new molecules expressed in plants, assays on in vitro alpha-amylase inhibitory activity applying the method using DNS (dinitrosalicylic acid) described by Bernfeld, 1955 (Bernfeld, P. In Methods Enzymology 1:149-158, 1955). The plant protein extracts were obtained as described above. 100 µg of total extract was used (quantified by the Bradford method) in the presence of the alpha-amylase enzyme of the boll weevil, diluted in buffer (0.15M succinic acid, 0.02 M CaCl2 and 0.06M NaCl, pH 4.5) totalizing the final volume of 50 µL. The quantity of enzyme used was the necessary to degrade 30 µg of maltose, defined as a unit of amylase activity (UA) corresponding to the increase of 0.1 in the OD 550 nm. Firstly, the incubation of the enzyme with the protein extract was conducted at 37° C. during 20 min. 50 µL of potato starch 1% dissolved in the activity buffer of the enzyme was added (described above) and incubated for 30 min at 37° C. Subsequently, 100 µL of DNS solution was added and the incubated reaction at 100° C. for 5 min. After the addition of 1 mL of water to the reading of the absorbance was determined using microplate reader (BioRad) at a wavelength of 550 nm. All the assays were performed in triplicate and the results obtained for the control using untransformed plant extracts or absence of proteins were considered to eliminate the effect of the endogenous amylase in the inhibition reaction. The level of inhibitory activity against boll weevil α-amylase observed for the analogous proteins varied from 36 to 75% (FIG. 11), according to the protein concentration present (determined in the ELISA assays) which varied from 3.9 to 11.7 nM (FIG. 10). The isolated bean inhibitors are: αAI-1 and αAI-2 do not show activity against *A. grandis* alpha-amylase (FIG. 11).

Example 4

Determination of the tertiary structure in silico of the complex containing the analogous of the α-amylase inhibitors: active αAIC3 (SEQ ID NO: 4) and αAIA11 (SEQ ID NO: 5) against *A. grandis* alpha-amylase.

The tertiary structures of the *A. grandis* alpha-amylase and the analogous αAIs were predicted in silico, being modeled by the molecular homology using as template the crystal structure of the complex containing the αAI-1 inhibitor and *Tenebrio molitor* alpha-amylase (1viw.pdb—Protein Database code) Nahoum, V.; Farisei, F.; Le-Berre-A., V.; Egloff, M. P.; Rouge, P.; Poerio, E.; Payan, F.; A Plant-seed inhibitor of two classes of alpha-amylases: x-ray analysis of *Tenebrio molitor* larvae alpha-amylase in complex with the bean *Phaseolus vulgaris* inhibitor. Acta Crystallography, 55-360, 1999) deposited in the database of the protein structure (PDB). The multiple sequence alignment containing the sequences of the mold structures and of the molecules to modeling was submitted for the Modeller Version 9.7 program (Sali A, Blundell TL: Comparative protein modeling by satisfaction of spatial restraints. Journal Molecular Biology, 234:779-815.1993). The models obtained by the Modeller program were visualized by the PyMOL program (Delano, W. L. The PyMOL Molecular Graphics System (2002) on World Wide Web http://www.pymol.org) and analyzed regarding its stereochemical properties by the PROCHECK program (Laskowski R A, Macarthur M W, Moss D S, Thornton J M: Procheck—a Program to Check the Stereochemical Quality of Protein Structures. Journal of Applied Crystallography 1993, 26:283-291). The αAIs inhibitors have two loops (n-terminal and c-terminal) (FIGS. 6, 7 and 12) the main ones involved with interaction specificity differences. A conformational change of said two loops could signficatively change the ability to interact with a certain enzyme, since they contribute with the major part of the interface with the enzyme. The structural representation of the *A. grandis* alpha-amylase model and of the analogous αAIC3 (SEQ ID NO: 4) and αAIA11 (SEQ ID NO: 5), overlapping and, in complex, indicates that the structural skeleton of the two molecules was maintained, being the differences observed only in amino acid side chains substituted in the analogous (FIG. 12). A visual analysis of the modeled structure confirms that all the residues that participate of said main interaction loop are present in the analogous αAIs. The identification of the residues involved in the interaction model interface was obtained in the server Protein-protein interaction (http://www. biochem.ucl.ac.uk/bsm/PP/server/). The formatted result in Table 1 correspond to the mutations found in the analogous alpha-amylase inhibitor in comparison to the original inhibitors αAI-1 and αAI-2, using the algorithm available in http://www.biochem.ucl.ac.uk/bsm/PP/server/. The residues shaded indicate amino acids identical to the primary sequence of the αAI-1, while the unshaded residues indicate amino acids of the αAI-2 sequence. Furthermore, the Table contains the number of hydrogen bonds (H Bonds) formed with each one of the residues, contribution estimates of the area which each residue occupates in the molecule surface, as the percentage which said area represents in the total complex (enzyme-inhibitor).

TABLE 1

Residues envolved in the interaction interface of the modeled structures of the enzyme-inhibitor complex (parental and mutant analogous) -

| Residue number αAI-1 | Residue name αAI-1 | Surface area | H bonds | % interface area | Residue number αAI-C3 | Residue name αAI-C3 | Surface area | H bonds | % interface area |
|---|---|---|---|---|---|---|---|---|---|
| 525 | TYR | 66 | 0 | 5 | 525 | TYR | 55 | 0 | 4 |
| 526 | ASN | 123 | 3 | 9 | 526 | ASN | 111 | 0 | 8 |

TABLE 1-continued

| 527 | SER | 24 | 0 | 2 | 527 | SER | 20 | 0 | 1 |
|---|---|---|---|---|---|---|---|---|---|
| 528 | TYR | 130 | 1 | 9 | 528 | TYR | 126 | 1 | 9 |
| 533 | ARG | 29 | 1 | 2 | 533 | ARG | 19 | 0 | 1 |
| 564 | HIS | 37 | 0 | 3 | 564 | HIS | 48 | 0 | 3 |
| 567 | ALA | 41 | 0 | 3 | 567 | ALA | 36 | 0 | 3 |
| 594 | LEU | 6 | 0 | 0 | 594 | LEU | 7 | 0 | 0 |
| 670 | THR | 20 | 0 | 1 | 670 | ILE | 29 | 0 | 2 |
| 673 | ALA | 25 | 0 | 2 | 673 | VAL | 43 | 0 | 3 |
| 674 | TYR | 170 | 3 | 12 | 674 | HIS | 133 | 0 | 10 |
| 675 | GLN | 65 | 0 | 5 | 675 | GLU | 63 | 0 | 5 |
| 676 | TRP | 15 | 1 | 1 | 676 | TYR | 20 | 0 | 1 |
| 678 | TYR | 96 | 3 | 7 | 678 | PHE | 87 | 0 | 6 |
| Total | | 847 | 12 | 61 | | | 797 | 1 | 56 |

Residues Al-1 AlC3 09
Residues Ai-2 AlC3 06

| Residue number αAl-1 | Residue number αAl-A11 | Residue name αAl-A11 | Surface area | H bonds | % interface area | Residue name αAl-2 |
|---|---|---|---|---|---|---|
| 525 | | | | | | |
| 526 | 524 | HIS | 33 | 0 | 2 | |
| 527 | 525 | THR | 18 | 0 | 1 | |
| 528 | 526 | VAL | 48 | 0 | 4 | |
| 533 | 531 | SER | 3 | 1 | 0 | |
| 564 | 562 | HIS | 36 | 0 | 3 | GLN |
| 567 | 565 | ALA | 35 | 0 | 3 | VAL |
| 594 | 592 | ARG | 43 | 0 | 3 | |
| 670 | 668 | THR | 19 | 0 | 1 | ILE |
| 673 | 671 | ALA | 23 | 0 | 1 | VAL |
| 674 | 672 | TYR | 164 | 3 | 12 | HIS |
| 675 | 673 | GLN | 63 | 0 | 5 | GLU |
| 676 | 674 | TRP | 17 | 0 | 1 | TYR |
| 678 | 676 | TYR | 94 | 2 | 7 | PHE |
| Total | | | 596 | 6 | 43 | |

Residues Al-1 Al A11 08
Residues Ai-2 Al A11 05

Figures 6, 7:
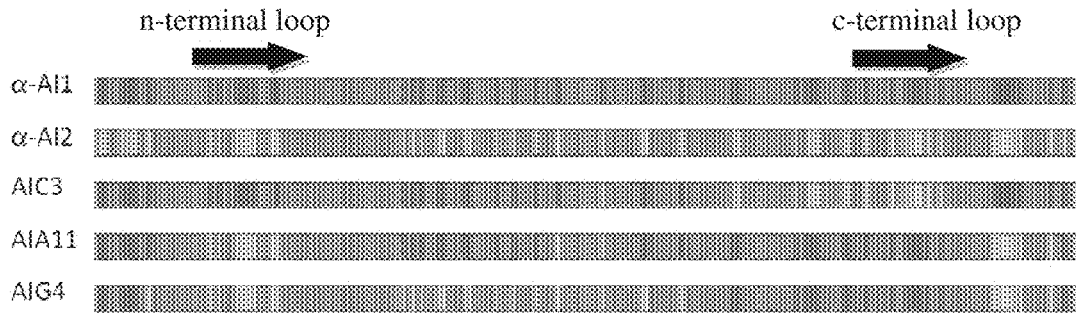
FIG. 6. Schematic representation showing the position of mutations in alignment. Analysis of the nucleotide base changes generated by the DNA Shuffling technique compared to the parental genes.
FIG. 7. The alignment of the protein sequences of the original and analogous mutant inhibitors AI1 (SEQ ID NO: 7); AI2 (SEQ ID NO: 8); AIC3 (SEQ ID NO: 4); AIA11 (SEQ ID NO: 5); and AIG4 (SEQ ID NO: 6). Illustrative scheme of the recombination profile of the analogous mutant genes selected from the combinatorial library. The numbers above the alignments are relative to the position of each nucleotide in the sequence. The sequences have been aligned by utilizing the program CLUSTALW2.
Figure 12:
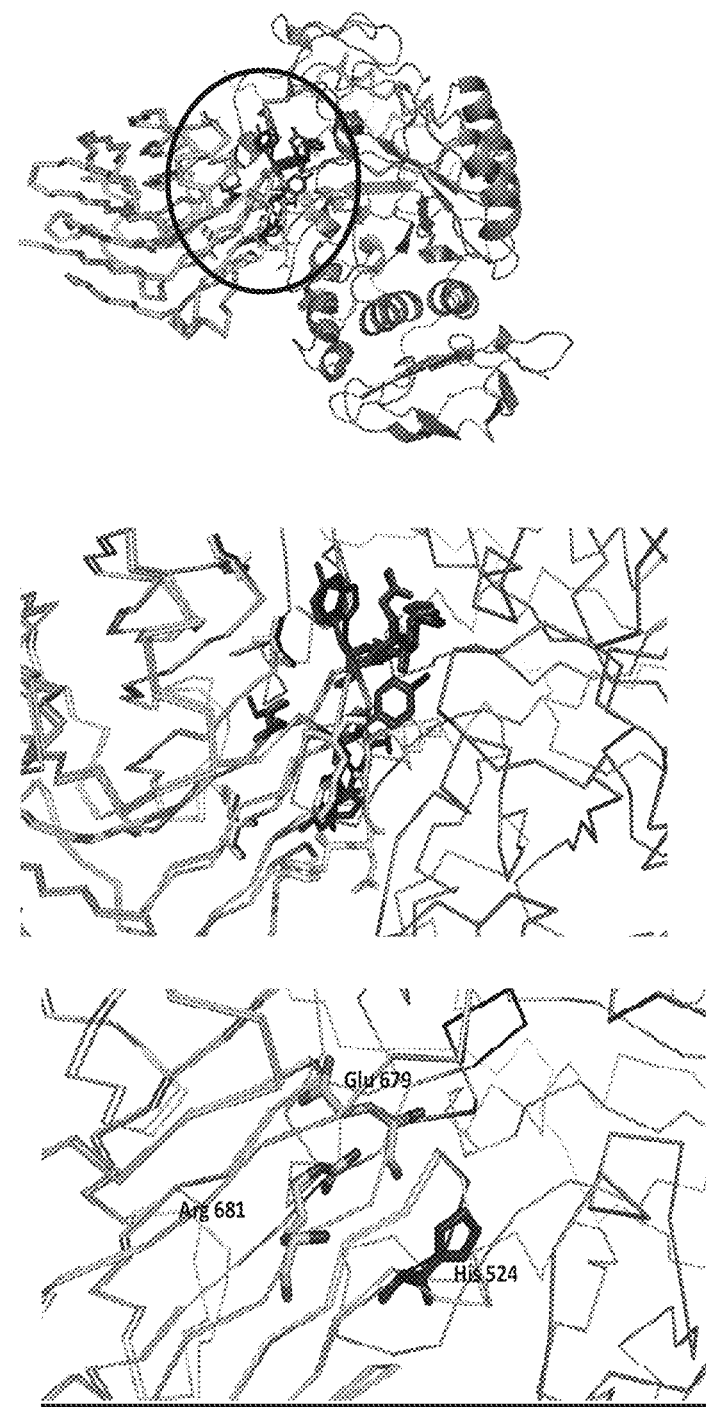
FIG. 12. Representation of the structure of the modeled complex containing αAI-C3 and αAI-A11 (overlapped) and *A. grandis* alpha-amylase.

It is observed that in relation to the two main loops of interaction (FIG. 6 and FIG. 7), that the αAIC3 mutant analogous (SEQ ID NO: 4) has sequence of the n-terminal loop identical to the αAI-1 inhibitor. In relation to the c-terminal loop, the αAIC3 analogous (SEQ ID NO: 4) present a sequence identical to αAI-2. In FIG. 12 containing the schematic representation of the structure of the modeled complex, it is possible to visualize the position of the residues mentioned in Table 1.

Nevertheless, as homology modeling, said complex has limitations in relation to the flexibility of the structure to be modeled on a mold, the modeled structure slightly differs of its own mold. The elucidation of differences in the structures involved in the inhibition creation in the mutant analogous for enzyme not inhibited by the original inhibitors depend on studies at a deeper level involving molecular dynamics. In this case, conditions are created wherein the structures can move freely and assume various conformations till they find the minimum free energy path, indicating a conformation that is more appropriate for the model. However, that kind of assay requires very long computational time and programming capability utilizing quantum energy.

The invention claimed is:

1. An isolated nucleic acid molecule comprising a nucleotide sequence selected from the group consisting of a)-c):
   a) a nucleotide sequence having at least 98% sequence identity to the nucleotide sequence of SEQ ID NO: 1;
   b) a nucleotide sequence having at least 99% sequence identity to the nucleotide sequence of SEQ ID NO: 2; and,
   c) a nucleotide sequence having at least 97% sequence identity to the nucleotide sequence of SEQ ID NO: 3.

2. A gene construct comprising the nucleic acid molecule of claim 1.

3. The gene construct of claim 2, wherein said gene construct further comprises a promoter sequence and a leader sequence, wherein said promoter sequence and said leader sequence are operably linked to said nucleic acid molecule.

4. The gene construct according to claim 3, wherein said promoter is selected from the group consisting of a constitutive promoter, an inducible promoter, and a tissue-specific promoter.

5. The gene construct according to claim 4, wherein said promoter is a tissue-specific promoter of a cotton fiber gene.

6. The gene construct according to claim 5, wherein said cotton fiber gene promoter is from a gene selected from the group consisting of E6, H6S, Rac13, LTP, ACP, Expansin, CAP, Annexin, FbL2A and Actin 2.

7. The gene construct according to claim 3, wherein said promoter sequence further comprises an enhancer element.

8. The gene construct according to claim 3, wherein said promoter is active in a host selected from the group consisting of plants, animals, bacteria, fungi and insects.

9. The gene construct according to claim 3, wherein said leader sequence and said promoter sequence are obtained from the same gene.

10. A binary vector comprising the gene construct according to claim 2.

11. A binary vector comprising the gene construct according to claim 3, wherein said binary vector further comprises a termination signal, a replication origin, a selection marker sequence, and a cloning site.

12. The binary vector according to claim 11, wherein the promoter is selected from the group consisting of a constitutive promoter, an inducible promoter and a tissue-specific promoter.

13. The binary vector according to claim 12, wherein said promoter is a tissue-specific promoter of a cotton fiber gene.

14. The binary vector according to claim 13, wherein said cotton fiber gene promoter is from a gene selected from the group consisting of E6, H6S, Rac13, LTP, ACP, Expansin, CAP, Annexin, FbL2A and Actin 2.

15. The binary vector according to claim 11, wherein said promoter sequence further comprises an enhancer element.

16. The binary vector according to claim 11, wherein the leader sequence and the promoter sequence are obtained from the same gene.

17. The binary vector according to claim 11, wherein said promoter is active in a host selected from the group consisting of plants, animals, bacteria, fungi and insects.

18. The binary vector according to claim 11, wherein the termination signal is selected from the group consisting of SV40 termination signal, HSV TK adenylation signal, nopaline synthethase gene termination signal of *Agrobacterium tumefasciens* (NOS), octopine synthethase gene termination signal, 19S and 35S gene termination signal of CaMV, gene termination signal of maize alcohol dehydrogenase, mannopine synthethase gene termination signal, beta-phaseolin gene termination signal, ssRUBISCO gene termination signal, sucrose synthetase gene termination signal; termination signal of the virus which attacks *Trifolium subterranean* (SCSV), and trpC gene termination signal of *Aspergillus nidulans*.

19. The binary vector according to claim 11, wherein the selection marker sequence confers resistance to an antibiotic, or is a visual marker.

20. The binary vector according to claim 19, wherein said selection marker sequence confers resistance to an antibiotic selected from the group consisting of kanamycin, neomycin, ampicillin, chloramphenicol, streptomycin, hygromycin, geneticin, phosphinothricin, glyphosate, and ammonium glufosinate; or is an AHA, BAR or GUS gene.

21. An isolated polypeptide encoded by the nucleic acid molecule of claim 1.

22. A transformed cell comprising the gene construct according to claim 2.

23. A transformed cell comprising the binary vector according to claim 10.

24. A transformed cell which expresses the polypeptide according to claim 21.

25. The transformed cell according to claim 22, wherein said cell is a bacterial cell, a fungal cell, an insect cell, a mammalian cell, or a plant cell.

26. A plant, or a part, propagule, or progeny thereof, comprising the gene construct according to claim 2.

27. A plant, or a part, propagule, or progeny thereof, comprising the binary vector according to claim 10.

28. A plant, or a part, propagule, or progeny thereof, which expresses the polypeptide according to claim 21.

29. A microorganism, or a part thereof, comprising the gene construct according to claim 2.

30. A microorganism, or a part thereof, comprising the binary vector according to claim 10.

31. A microorganism, or a part thereof, which expresses the polypeptide according to claim 21.

32. A method for producing a transgenic organism, comprising the following steps:
   a. transforming a cell, tissue, organ or embryo with the gene construct according to claim 2;
   b. selecting transformed cells, callus cells, embryos or seeds;
   c. growing mature plants, mature embryos or transformed microorganisms, from the callus cells, embryos or seeds selected in step (b); and
   d. selecting mature plants, mature embryos or microorganisms produced in step (c), containing said gene construct.

33. A method for producing recombinant protein, comprising the following steps:
   a. transforming a cell, tissue, organ or embryo with the binary vector according to claim 10;
   b. selecting transformed cells, callus cells, embryos or seeds;
   c. growing mature plants, mature embryos or transformed microorganisms, from the callus cells, embryos or seeds selected in step (b);
   d. selecting mature plants, mature embryos or microorganisms produced in step (c), containing said binary vector; and
   e. extracting recombinant protein produced by the organisms selected in step (d).

34. A recombinant protein obtained by the method of claim 33.

35. A biodegradable pesticidal composition, wherein said composition comprises an effective concentration of the polypeptide according to claim 21, in an agronomically acceptable carrier.

36. The biodegradable pesticidal composition according to claim 35, wherein the acceptable carrier is a transformed microorganism.

37. The biodegradable pesticidal composition according to claim 35, wherein the acceptable carrier is selected from the group consisting of a surface-active agent, an inert carrier, a preservative, a humectant, a feeding stimulant, an attractant, an encapsulating agent, a binder, an emulsifier, a colorant, an UV shield (ultraviolet), a buffer, a flow agent or fertilizer, and micronutrient donors.

38. The biodegradable pesticidal composition according to claim 35, wherein said composition further comprises a Bt δ-endotoxin.

39. A method for controlling a pest, comprising the following steps:
   a) detecting the occurrence of the pest in an environment;
   b) promoting the contact of the pest with the polypeptide of claim 21.

40. A method for producing a transgenic line resistant to an insect pest, comprising the following steps:
   a) transforming a cultivar of interest with the gene construct according to claim 2;
   b) growing transgenic lines containing said construct stably integrated into their genomes; and
   c) selecting a transgenic line expressing the polypeptide encoded by said gene construct.

* * * * *